(12) United States Patent
Connor

(10) Patent No.: US 10,058,278 B2
(45) Date of Patent: Aug. 28, 2018

(54) SYSTEMS AND METHODS FOR MONITORING PRESSURE APPLIED ON PATIENTS

(71) Applicant: ANAESTHESIA ASSOCIATES OF MASSACHUSETTS, P.C., Westwood, MA (US)

(72) Inventor: Christopher William Connor, Arlington, MA (US)

(73) Assignee: ANAESTHESIA ASSOCIATES OF MASSACHUSETTS, P.C., Westwood, MA (US)

( * ) Notice: Subject to any disclaimer, the term of this patent is extended or adjusted under 35 U.S.C. 154(b) by 144 days.

(21) Appl. No.: 13/652,099

(22) Filed: Oct. 15, 2012

(65) Prior Publication Data
US 2013/0102930 A1  Apr. 25, 2013

Related U.S. Application Data

(60) Provisional application No. 61/546,706, filed on Oct. 13, 2011.

(51) Int. Cl.
*A61B 5/00* (2006.01)
*A61B 1/267* (2006.01)
*A61B 5/103* (2006.01)
*A61M 16/04* (2006.01)
*G01L 1/20* (2006.01)

(52) U.S. Cl.
CPC .............. *A61B 5/447* (2013.01); *A61B 1/267* (2013.01); *A61B 5/0002* (2013.01); *A61B 5/103* (2013.01); *A61B 5/6822* (2013.01); *A61B 5/6832* (2013.01); *A61B 5/72* (2013.01); *A61B 5/742* (2013.01); *A61M 16/04* (2013.01); *G01L 1/20* (2013.01); *A61B 2562/0247* (2013.01)

(58) Field of Classification Search
USPC ......................................................... 600/590
See application file for complete search history.

(56) References Cited

U.S. PATENT DOCUMENTS 5,361,753 A * 11/1994 Pothmann ........... A61M 16/044
                                                               128/202.22
6,165,142 A * 12/2000 Bar ............................... 600/595
(Continued)

FOREIGN PATENT DOCUMENTS

GB        2445760 A       7/2008
WO     WO-0271930 A1     9/2002

OTHER PUBLICATIONS

International Search Report for PCT/US2012/060247 dated Jan. 7, 2013.

*Primary Examiner* — Daniel Cerioni
*Assistant Examiner* — Yasmeen S Warsi
(74) *Attorney, Agent, or Firm* — Haley Guiliano LLP

(57) ABSTRACT

The systems and methods described herein are directed to monitoring the force or pressure applied to a portion of the human body, including in the neck region of a patient during a medical procedure, such as tracheal intubation, to ensure that the medical personnel are applying the desired level of force, and in regions of bony prominences to monitor and prevent the formation of pressure ulcers or decubitus ulcers. In particular, the systems and methods described herein include piezoresistive elements connected to signal processing circuitry for measuring the force or pressure.

31 Claims, 15 Drawing Sheets

(56) References Cited

U.S. PATENT DOCUMENTS

| | | | |
|---|---|---|---|
| 7,794,412 B2 * | 9/2010 | Turnbull et al. | 600/587 |
| 2008/0278336 A1 * | 11/2008 | Ortega et al. | 340/573.5 |
| 2010/0152619 A1 | 6/2010 | Kalpaxis et al. | |
| 2011/0084346 A1 | 4/2011 | Mori | |
| 2013/0211590 A1 * | 8/2013 | Diolaiti | B25J 9/1689 700/257 |
| 2013/0281885 A1 * | 10/2013 | Rowbottom | A61B 5/0215 600/587 |

* cited by examiner

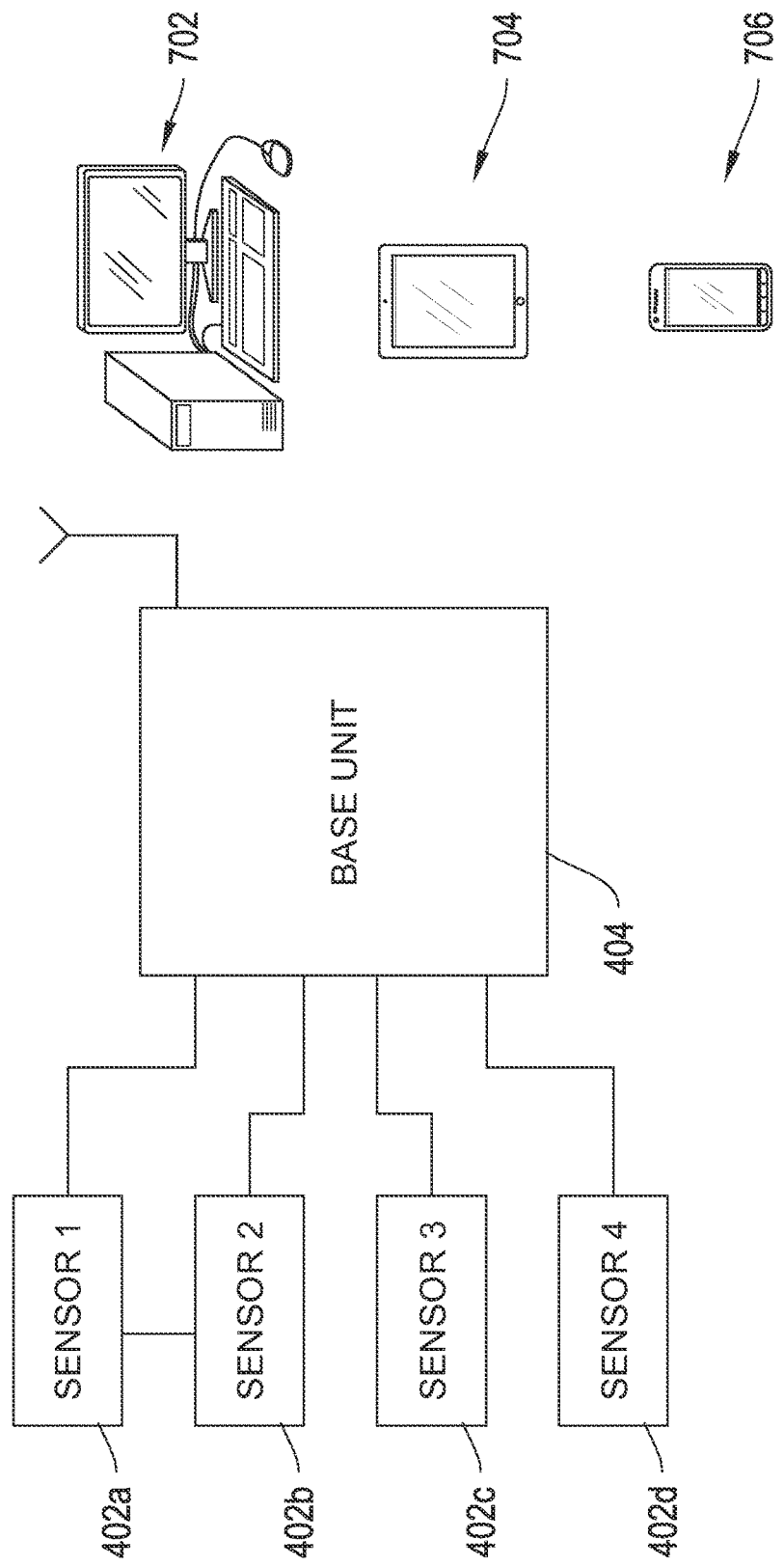

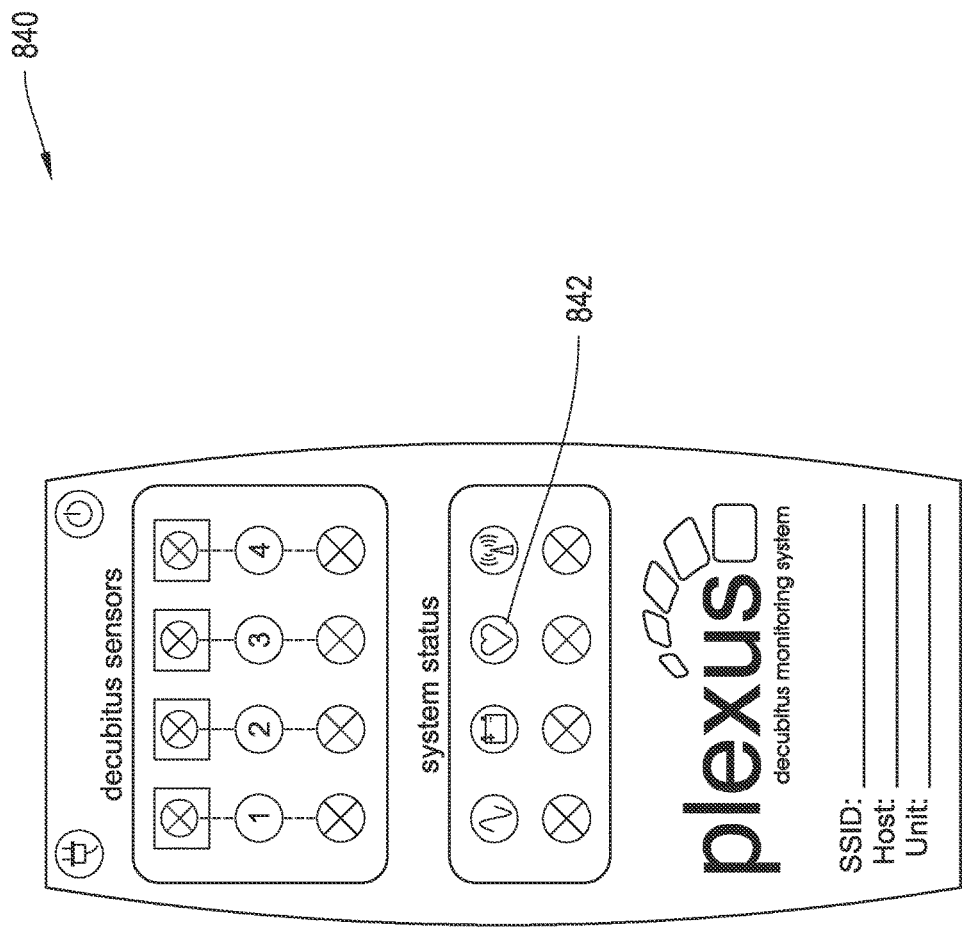

SYSTEMS AND METHODS FOR MONITORING PRESSURE APPLIED ON PATIENTS

CROSS-REFERENCE TO RELATED APPLICATIONS

This application claims the benefit of U.S. Provisional Application 61/546,706 filed Oct. 13, 2011, the contents of which are incorporated by reference herein in their entirety.

BACKGROUND

Medical personnel frequently perform intubation of the trachea with an endotracheal tube. Tracheal intubation is frequently performed in critically injured, ill or anesthetized patients to facilitate ventilation of the lungs, including mechanical ventilation, and to prevent the possibility of asphyxiation or airway obstruction. Tracheal intubation typically includes the placement of a flexible plastic tube into the trachea (windpipe) to maintain an open airway or to serve as a conduit through which to administer certain drugs. Because it is an invasive and uncomfortable medical procedure, intubation is usually performed after administration of general anesthesia and a neuromuscular-blocking drug, which typically require the patient to not have a full-stomach.

In certain situations, such as emergency situations, the medical personnel will not know if the patient has a full-stomach. In such situations, the medical personnel use procedures to minimize the possibility of regurgitation and pulmonary aspiration of gastric contents during the induction of general anesthesia and subsequent tracheal intubation. Regurgitation and pulmonary aspiration of gastric contents can cause severe inflammation of the lungs and consequently, can be fatal. One method to reduce this risk is to secure the airway by employing a rapid sequence intubation (RSI) technique utilizing general anesthesia medications. One key feature of RSI is the application of manual force or pressure to the neck region, particularly the cricoid cartilage, often referred to as the "Sellick maneuver", prior to instrumentation of the airway and intubation of the trachea. Applying the necessary force causes the esophagus to occlude while still keeping the airway open.

However, too much or too little force may put the patient at risk. Too much force may damage the trachea or other surrounding anatomical structures or may result in inadequate patient ventilation. Too little force may undermine the efficacy of the procedure by failing to occlude the esophagus and prevent aspiration of gastric contents. Because of the importance of the amount of force, the person applying the pressure must know how to do so properly. Even a trained medic, however, cannot always apply and maintain the proper pressure without some method of monitoring the force being applied.

In addition to pressure-related difficulties arising in connection with medical personnel applying the appropriate amount of pressure on patients during a procedure, in certain medical situations, pressure-related difficulties may arise from patients developing ulcers from the application of prolonged pressure on regions of bony prominence. Pressure ulcers are typically lesions caused by unrelieved pressure that results in damage to underlying tissue. If pressure is applied to the region of bony prominence, and if the pressure is maintained for a prolonged period of time, this pressure can lead to breaking of the person's skin, reduced blood flow to the skin, surface and subsurface tissue and necrosis of epithelial tissue. These pressure ulcers can develop, for example, in persons who are bed-ridden or confined to a wheelchair. Current techniques for reducing the risk of ulcer formation range from diligent nursing protocols for ensuring patients are moved periodically, to equipments such as overlays, mattresses, specialized beds and complicated pressure monitoring systems designed to limit pressure on certain portions of the human body.

SUMMARY

The systems and methods described herein are directed to computerized monitoring of force applied to a body part either by a medical personnel or by the patient applying weight to a region of bony prominence. In one example, the systems and methods described herein are directed to monitoring force applied during laryngeal manipulation procedures like the Sellick Maneuver. Manipulating the laryngeal region by applying force or pressure is the standard of care in the anesthesia community. As noted above, too much, or too little force may place the patient at risk. Approximately, 20-40 Newtons (N) of cricoid force is necessary to achieve esophageal occlusion, which effectively prevents regurgitation of gastroesophageal contents into the lungs of the patient. In terms of Newton's (N), the recommended force to be exerted before loss of consciousness is 20 N, or approximately 2 kg of force. The force is then increased to between 30 to 40 N, or 3 kg to 4 kg of force for an unconscious person. The systems and methods described herein are directed to monitoring the force or pressure applied in the neck region of a patient during a medical procedure, such as tracheal intubation, to ensure that the medical personnel are applying the desired level of force. In particular, the systems and methods described herein include piezoresistive elements connected to signal processing circuitry for measuring the force applied by medical personnel and indicating whether more or less force is needed.

In another example, the systems and methods described herein are directed to monitoring and preventing the formation of pressure ulcers when patients apply pressure to a region of bony prominence over a prolonged period of time. Pressure ulcers are typically caused by different tissue forces, including pressure, or the compression of tissues and/or destruction of muscle cells. This compression is generally caused by the unrelieved force of bone against a surface, as when a patient remains in a single decubitus position for a lengthy period. After an extended amount of time with decreased tissue perfusion, ischemia occurs and can lead to tissue necrosis if left untreated. Pressure can also be exerted by external devices, such as medical devices, braces, wheelchairs, etc. Other external factors such as friction shear and moisture are considered factors influencing the formation of pressure ulcers. Not to be bound by theory, but normal arteriole, capillary, and venule pressures are about 30, 20 and 12 mm of Hg, respectively. Excess pressure (i.e., above 32 mm of Hg) may result in occlusion of capillary flow causing ischemic injury and extravasation of fluids, cells, and protein. Muscle can be damaged by pressures exceeding 60 mm of Hg for more than an hour or so. The standard of care in hospitals and medical facilities is to frequently reposition patients every 2-hours or so. The systems and methods described herein are directed to monitoring the force or pressure applied in regions of bony prominence to prevent the formation of pressure ulcers or decubitus ulcers, and alert medical personnel when a patient may need repositioning or when the likelihood of ulcer formation exceeds a threshold. In particular, the systems and methods described herein include piezoresistive elements connected to signal processing circuitry for measuring and monitoring the pressure on regions of bony prominences.

Although the systems and methods described herein will be discussed with reference to systems and applications adapted to monitor the application of pressure on the cricoid cartilage or the neck region, or on the application of pressure on regions of bony prominences, it will be understood that these systems and methods may be employed to help any individual monitor and visualize information about applied force or pressure. In general, during medical procedures or surgery, doctors, nurses, and other medical personnel are called on to apply pressure on a part of a patient's internal or external anatomy. For example, during a coronary catheterization, force may need to be applied to the groin region at the level of the femoral vessels. Similarly, force may need to be applied during other less invasive cardiac procedures. In such medical procedures, pressure or force may need to be applied and sustained for extended periods of time. Failure to maintain the appropriate pressure for the appropriate amount of time can lead to the formation of hematoma around the vessels, which can potentially compromise circulation to the affected limb. Accordingly, it is an advantage of this technique to allow the medical personnel to monitor and visualize the pressure they apply when performing a procedure. In some instances, the pressure or force information may be sent to a third party to track and monitor.

Although the technique will be referred to hereinafter with reference to "force" it should be appreciated that the technique is also commonly referred to with reference to "pressure." Thus, "force" as used herein is to be interpreted as encompassing "pressure" and vice versa except where such an interpretation would be contrary to the contextual meaning.

More particularly, in certain aspects, the systems and methods described herein include systems for monitoring force applied during laryngeal manipulation. The systems may include a force responsive element and a base unit, which may be disposed within a housing. The force responsive element may have a property which varies with the applied force, and may be configured to be positioned on a neck region of a patient. The base unit may be connected to the force responsive element and may have circuitry for determining an amount of force applied based on a value of the property of the force responsive element. In certain embodiments, the neck region may include an anterior portion of the neck such as a region inferior to the thyroid cartilage or near the cricoids cartilage.

In certain embodiments, the force responsive element includes one or more force sensitive resistor. In particular, the force sensitive resistor may include a resistive layer, a conductive layer and a spacer layer positioned between the resistive layer and the conductive layer. The conductive layer may include at least two unconnected conductive traces disposed on a flexible substrate, and the resistive layer may be disposed over a gap between the at least two conductive traces. In certain embodiments, the resistive layer is formed from piezoresistive material. The force responsive element may further include at least one of an adhesive layer and a padding layer.

The force responsive element may include two force responsive elements physically attached to one another. In particular, a portion of the two force responsive elements may be separated by a distance substantially similar to a distance along a curvature of the neck region on either side of a cricoid cartilage of the patient.

In certain embodiments, the property of the force responsive element may include at least one of an electrical property, magnetic property, optical property, physical property, and chemical property. In particular, the property may include at least one of electrical resistance, capacitance and inductance. The property may increase or decrease, linearly or non-linearly, with increasing the applied force. The property may vary only within a range of applied forces. The force responsive element may include an attachment mechanism, such as an adhesive, for positioning on the neck region of the patient. The force responsive element may be sized to accommodate at least a tip region of a finger.

The base unit may include signal processing circuitry for determining the value of the property, and display circuitry for displaying the amount of force applied. The signal processing circuitry may include circuitry for converting the value of the property to at least one of a voltage and current. In certain embodiments, the signal processing circuitry includes circuitry for amplifying at least one of the voltage and current. The display circuitry may include circuitry for displaying at least one of the voltage and current. Generally, the signal processing circuitry includes one or more operational amplifiers, and the display circuitry includes one or more light emitting diodes. In one example, the display circuitry includes four light emitting diodes corresponding to four ranges of the amount of force applied. The base unit may be connected to the force responsive element via a wireless or a wired connection. Additionally and optionally, the base unit may include a wireless transceiver and may be connected to a network for storing and sending data in connection with the amount of force applied on the force responsive element.

In another aspect, the systems and methods described herein may include a system for monitoring force applied on a force sensing element during laryngeal manipulation. The system may include a housing, signal processing circuitry disposed within the housing and configured to generate an electrical signal representative of a force applied on the force sensing element, and display circuitry, disposed at least partially on an outer surface of the housing, having one or more visual indicators for converting the electrical signal to an optical signal.

In certain aspects, the systems and methods described herein include a system for monitoring and preventing the occurrence of pressure ulcers in patients. The systems may include at least one force sensitive resistor, configured to be positioned (and optionally attached with adhesive) over a region of bony prominence on a patient, and having an electrical resistance which varies with the applied force. The region of bony prominence may include at least one of sacrum, coccyx, heel, hip, ankle, buttock, earlobe, occiput, chin, elbow, scapula, and knee. The at least one force sensitive resistor may include a resistive layer formed from piezoelectric material, a conductive layer, and a spacer layer positioned between the resistive layer and the conductive layer. In certain embodiments, the resistance decreases with increasing the applied force. The systems may also include a base unit (which may be disposed within a housing), connected to the force responsive element and having circuitry for determining an amount of force applied based on a value of the electrical resistance of the force sensitive resistor.

In certain embodiments, the conductive layer includes at least two unconnected conductive traces disposed on a flexible substrate, and the resistive layer is disposed over a gap between the at least two conductive traces. The systems described herein may comprise a plurality of force sensitive resistors, each configured to positioned over different regions of bony prominence on the patient. The force sensitive resistor may further include at least one of an adhesive layer and a padding layer. In certain embodiments, the force sensitive resistor includes or is combined with a material applicable to the patient's skin. For example, the force sensitive resistor is attached to a portion of the dressing, which is then applied to the patient's skin.

The base unit may include signal processing circuitry for determining the value of the electrical resistance, and display circuitry for displaying the amount of force applied. The signal processing circuitry may include circuitry for converting the value of the electrical resistance to at least one of a voltage and current. In certain embodiments, signal processing circuitry includes one or more operational amplifiers and may include circuitry for amplifying at least one of the voltage and current.

In certain embodiments, the display circuitry includes circuitry for displaying at least one of the voltage and current, including one or more light emitting diodes. The display circuitry may include one or more light emitting diodes for indicating system status including at least one of power status, wireless connectivity status, battery life, and signal status. The one or more light emitting diodes may be configured to illuminate in response to the at least one force sensitive resistor in operation on the patient. The one or more light emitting diodes may be configured to indicate that pressure applied on the at least one force sensitive resistor is greater than a predetermined threshold.

The signal processing circuitry may include circuitry for receiving electrocardiogram (EKG) signals from one or more EKG sensors. In certain embodiments, the display circuitry includes one or more light emitting diodes for indicating the status of at least one of the EKG signals and EKG sensors. When the system includes two force sensitive resistors, each may be connected to the base unit, and the base unit may include display circuitry configured to indicate a status of the two force sensitive resistors. Generally, the base unit may be configured with circuitry to receive signals from a plurality of force sensitive resistors.

The base unit may include wireless communication circuitry for transmitting data including at least one of the value of the electrical resistance of the force sensitive resistor, a voltage value determined based on the electrical resistance, an electric current value determined based on the electrical resistance, and the amount of force applied. The wireless communication circuitry may be configured to transmit the data at periodic intervals of time. The base unit may include pre-processing circuitry for averaging the data over a pre-determined window of time. The base unit may be connected to a network for sending and storing data about the amount of force applied. The base unit may be connected to the force sensitive resistor via wired or wireless connection.

In certain embodiments, the systems may further comprise a computer station having a processor including circuitry for receiving, from the base unit, pressure information corresponding to the force applied on the at least one force sensitive resistor. The processor may include a display and display circuitry for displaying, on the display, a visual indicator identifying the at least one force sensitive resistor. The display circuitry at the processor may include one or more visual indicators for indicating whether pressure applied on the at least one force sensitive resistor is greater than a predetermined threshold. In certain embodiments, display circuitry at the processor may include one or more visual indicators for indicating time during which pressure applied on the at least one force sensitive resistor is greater than a predetermined threshold. The visual indicator may include a plurality of colors, each color representative of the pressure applied on the at least one force sensitive resistor. The processor may include a display and display circuitry for displaying the location of the at least one force sensitive resistor on the patient.

In certain embodiments, the display circuitry includes one or more visual indicators for identifying the at least one force sensitive resistor, and for indicating whether pressure applied on the at least one force sensitive resistor is greater than a predetermined threshold. In particular, determining whether the pressure applied is greater than a predetermined threshold may include determining whether the pressure is greater than the predetermined threshold for a predetermined period of time.

The display may include a touch screen display that allows a user to setup the operation of at least one of the force sensitive resistor and the base unit. The touch screen display and the processor may be configured to allow a user to visually manipulate a location of the force sensitive resistor on a visual description of the patient on the display.

In another aspect the systems and methods described herein may include methods for monitoring and preventing the occurrence of pressure ulcers in patients. The methods may include providing a force responsive element, having a property which varies with the applied force, configured to be positioned over a region of bony prominence on a patient, and a base unit, connected to the force responsive element and having circuitry for determining an amount of force applied based on a value of the property of the force responsive element. The methods may further include establishing a wireless connection between the base unit and a computer station having a processor and a display, and displaying on the display a user interface including a visual representation of at least one of the location of the force responsive element on the patient, the status of the force responsive element, the amount of force applied on the force responsive element, and a cumulative amount of force applied on the force responsive element over a predetermined period of time.

In another aspect, the systems and methods described herein may include methods for monitoring and preventing the occurrence of pressure ulcers in patients. The methods may include disposing a force responsive element, having a property which varies with the applied force, over a region of bony prominence on a patient, and providing a base unit, connected to the force responsive element and having circuitry for determining an amount of force applied based on a value of the property of the force responsive element. The methods may include measuring, at the base unit, the amount of force applied over the region of bony prominence on the patient, sending data corresponding to the amount of force applied to a computer station, and determining, at the computer station, whether the amount of force applied over a predetermined period of time is greater than a predetermined threshold. In response to determining that the amount of force applied is greater than the predetermined threshold over the period of time, the methods may include generating an alarm signal to alert a medical personnel.

In still another aspect, the systems and methods described herein may include a system for monitoring and preventing the occurrence of pressure ulcers in patients, comprising. The systems may include a force responsive element, having a property which varies with the applied force, configured to be positioned over a region of bony prominence on a patient, and a base unit, connected to the force responsive element and having circuitry for determining an amount of force applied based on a value of the property of the force responsive element. In addition, the systems may include a computer station having a processor including circuitry for receiving, from the base unit, pressure information corresponding to the force applied on the at least one force responsive element, and displaying to a user information related to at least one of the patient and the measured pressure.

BRIEF DESCRIPTION OF THE DRAWINGS

The foregoing and other objects and advantages of the disclosure will be appreciated more fully from the following further description thereof, with reference to the accompanying drawings. The skilled person in the art will understand that the drawings, described below, are for illustration purposes only. The drawings are not intended to limit the scope of the applicant's teaching in any way.

FIG. 7 depicts a block diagram of a pressure monitoring system, according to an illustrative embodiment of the invention.

FIGS. 8A-8c depict exemplary base units, according to an illustrative embodiment of the invention.

DETAILED DESCRIPTION

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

Figure 1:
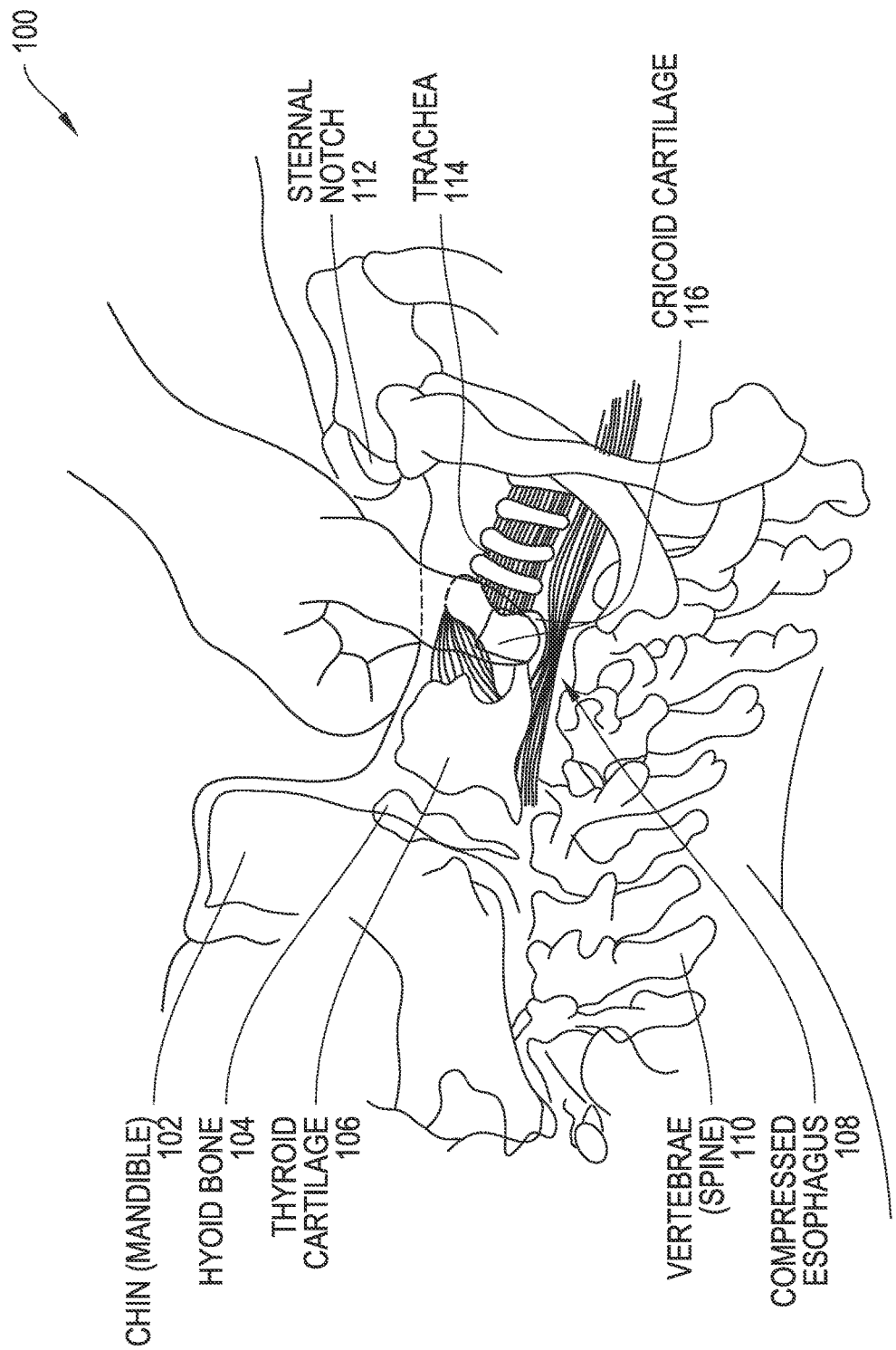
FIG. 1 depicts the application of force, during a medical procedure, on the anatomical structure of a neck region.

FIG. 1 depicts the application of force on the anatomical structure of the neck region. The neck region includes the cricoid cartilage 116 inferior to the thyroid cartilage 106 and posterior to the trachea 114. Typically, during tracheal intubation a plastic tube is placed into the trachea 114 to maintain an open airway or to serve as a conduit through which to administer certain drugs. As noted above, the "Sellick Maneuver" or the application of pressure to the cricoid cartilage 116 involves medical personnel pressing against the cricoid cartilage 116 thereby squeezing and occluding the esophagus 108. The maneuver prevents regurgitation of gastric contents during tracheal intubation.

Similarly, other techniques are performed by medical personnel to either clear a patient's airway or occlude the esophagus. For example, certain techniques include the application of force or pressure over the hyoid cartilage 104, larynx, or thyroid cartilage 106. Generally, these techniques involve the application of pressure on the neck or laryngeal anatomy. Certain other techniques involve the movement or manipulation of the neck or laryngeal anatomy. For example, the "BURP" maneuver, developed to improve the glottic view during endotracheal intubation, involves the backward, upward, and right-sided pressure on the thyroid and cricoid cartilages (106 and 116 respectively). In another example, the modified "BURP" maneuver involves the patient lying supine in a sniffing position. In the modified "BURP" maneuver, the thumb and middle finger are applied to the cricoid cartilage 116 and the index finger is applied to the left hand side of the thyroid cartilage 106. Pressure may be applied to both of these structures, downwards, superiorly, and to the right hand side.

When performing these procedures, as noted above, too much force or too little force on the neck region can be fatal for patients. Advantageously, the systems and methods described herein are directed to systems for monitoring and visualizing the pressure applied during laryngeal manipulation so that medical personnel can adjust the amount of pressure being applied in the neck region. The systems and methods described herein may be used in connection with any suitable laryngeal manipulation technique and for any suitable purpose such as preventing regurgitation and improving laryngoscopic view. The systems and methods described herein may be used in connection with any technique for applying pressure or manipulating any part of the human or animal internal or external anatomy, without departing from the scope of the invention.

Figure 2:
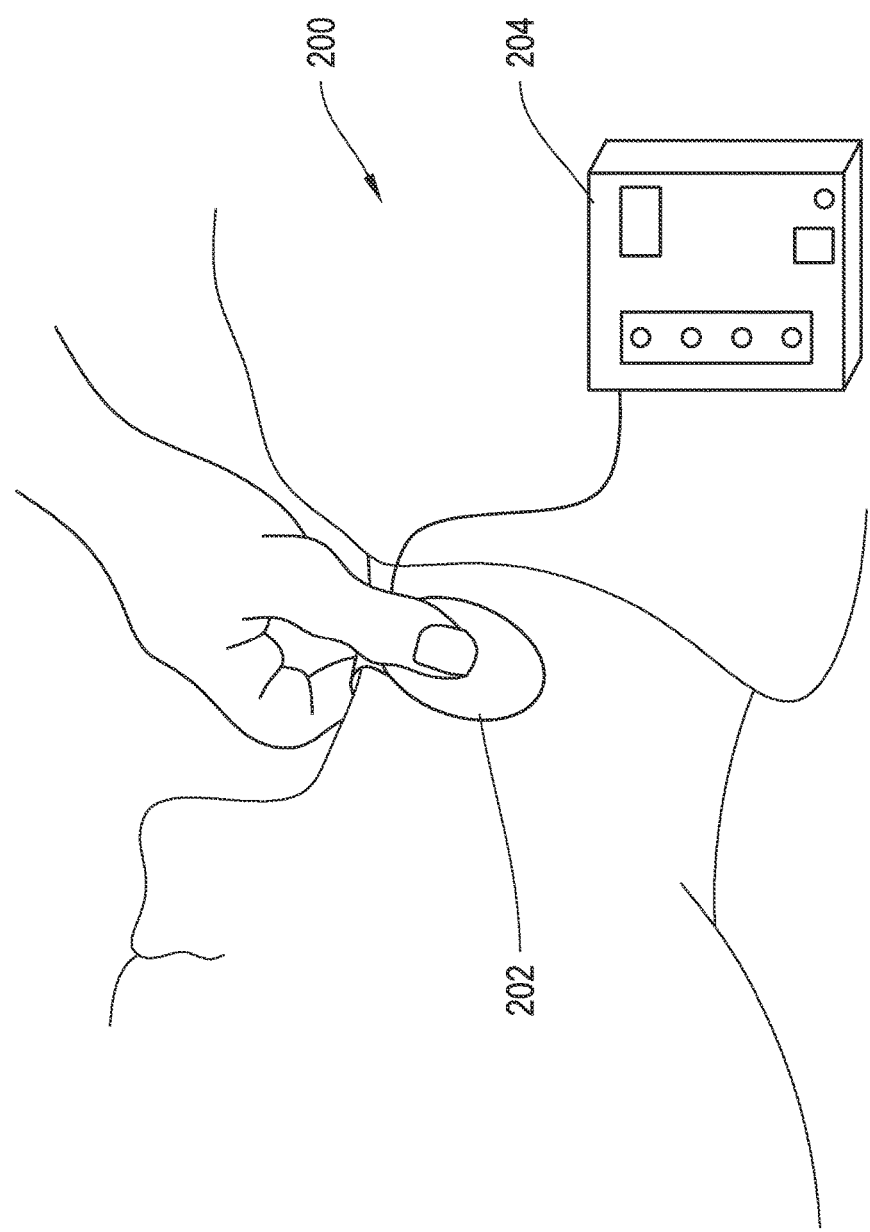
FIG. 2 depicts the application of force on the anatomical structure of a neck region, using a force monitoring system, according to an illustrative embodiment of the invention.

Turning now to FIG. 2, the systems and methods described herein include a system 200. The system 200 includes a force responsive element 202 and a base unit 204. In the embodiment shown in FIG. 2, the force responsive element 202 is positioned on a patient's neck region such that medical personnel may apply pressure on a portion of the neck region via the force responsive element 202. The force responsive element 202 is connected to the base unit 204. The base unit 204 typically includes circuitry for translating the force applied by the user to an electrical signal and consequently a visual signal, which can then be displayed using indicators on the base unit 204.

During operation of system 200, medical personnel may place the force responsive element 202 on a part of the anatomy, such as the neck region. When performing the Sellick Maneuver, the medical personnel may place the force responsive element 202 on the cricoid cartilage. In this example, the cricoid cartilage is generally located inferior to the thyroid cartilage. The cricoid cartilage can be pressed from either or both sides of the neck. In certain embodiments, the force responsive element 202 may be sized and shaped such that it may be extend to both sides of the neck and the user (e.g., medical personnel) may use their index finger on one side and their thumb on the other side and press against the cricoid cartilage.

Once the user presses against the cricoid cartilage, the force responsive element 202 may have a property which varies with the applied force. In one example, the force responsive element 202 may include materials having an electrical property, such as resistance, that varies with applied force. Base unit 204 includes circuitry such that the change in resistance of the force responsive element 202 may cause one or more light emitting diodes (LED). Depending on the amount of applied force, one or more LEDs may light up thereby informing the user or medical personnel about the amount of pressure being applied on the cricoid cartilage. The base unit 204 may include other suitable circuitry and visual indicators to provide force or pressure information to the user as desired.

Figure 3:
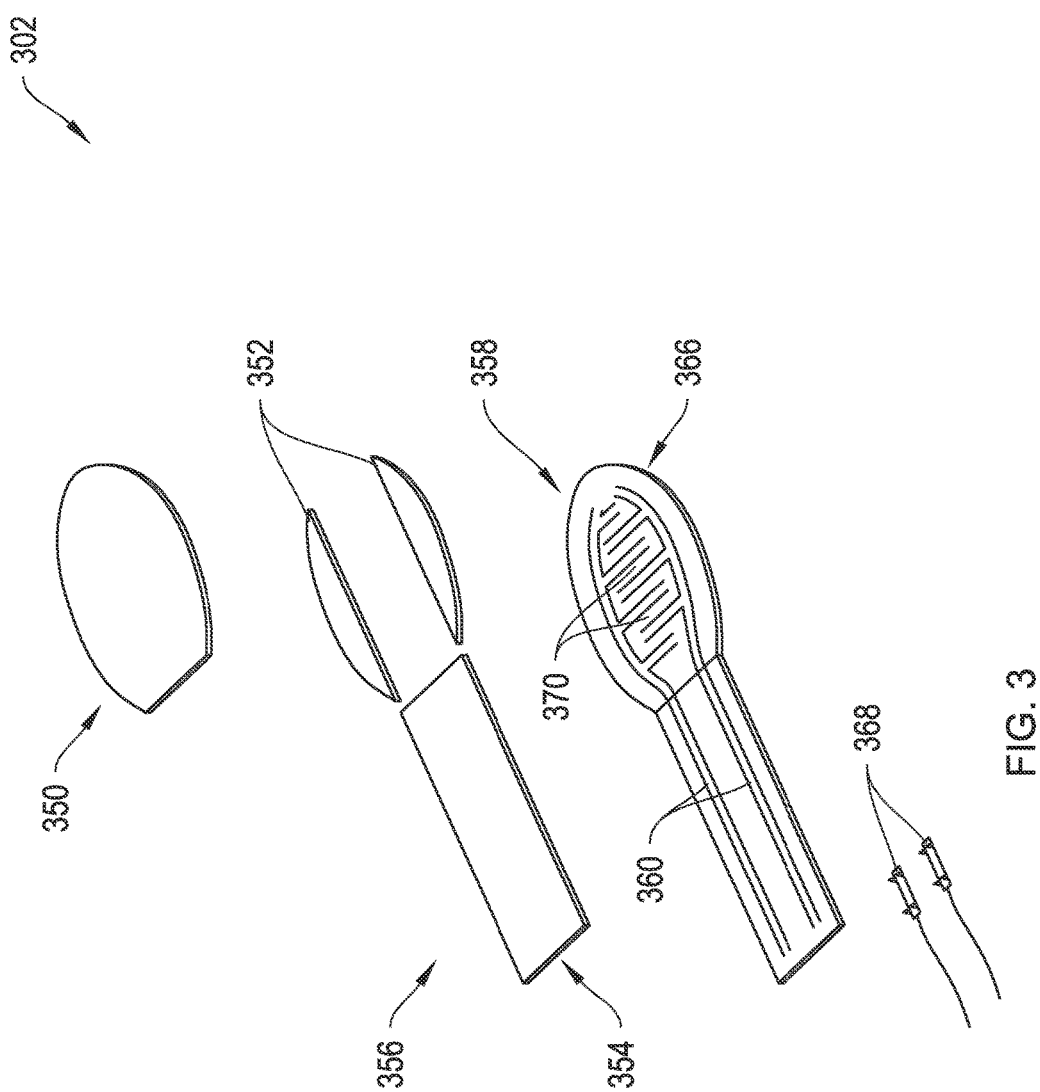
FIG. 3 depicts an exploded view of a force responsive element, according to an illustrative embodiment of the invention.

FIG. 3 depicts an exploded view of a force responsive element 302. Force responsive element 302 may be similar to force responsive element 202. As shown in FIG. 3, force responsive element 302 includes a force sensitive resistor. In particular, force responsive element 302 includes a resistive layer 350, a conductive layer 366 and one or more spacer layers 356 having spacer element 354 and adhesive 352.

In certain embodiments, resistive layer 350 may include one or more materials having a property which varies with applied force. The resistive layer 350 may include materials having an electrical property, such as electrical resistance, that varies with applied force. Such materials typically include a conductive elastomer or polymer or foam-like material. These materials typically include both electrically conducting and non-conducting particles suspended in matrix. The particles are sub-micrometer sizes, and are formulated to reduce the temperature dependence, improve mechanical properties and increase surface durability. Applying a force to the surface of the sensing film typically causes particles to touch the conducting electrodes, changing the resistance of the film. In certain embodiments, the resistive layer 350 includes carbon doped rubber materials.

The resistive layer 350 may be sized and shaped as suitable for the medical procedure being performed, the anatomical feature on which pressure is being applied, characteristics of the user's finger, or any other suitable requirement. For example, in the case of laryngeal manipulation, the resistive layer may be sized to accommodate a medical personnel's thumb and index finger. Generally, the resistive layer 350, and the force responsive element 302 may have any length, width, diameter, thickness and shape as desired.

To measure the variable resistance, and thereby the applied force, across the resistive layer 350, the force sensitive element 302 includes a conductive layer 366 attached to the resistive layer 350. Conductive layer 366 includes one or more conductive traces 360 disposed on a suitable substrate 358. The conductive traces 360 may be connected to an electrical circuit in a base unit (such as base unit 204) to complete the circuit. Conductive layer 366 may include a plurality of conductive traces 360 arranged in a suitable pattern such that there is a gap 370 between the traces 360. When the resistive layer 350 is disposed on top of the conductive layer 366 the conductive traces 360 are connected to each other via the resistive layer 350. The conductive traces 360 may be arranged in any suitable pattern such as a comb-structure or a grid-structure. The substrate 358 may be formed from any suitable electrically insulating material such as a printed circuit board FR4 material. The substrate 358 may be formed from flexible material such that the entire force sensitive resistor 302 may be flexible. Flexibility may be useful when the force sensitive element 302 is used in connection with the laryngeal manipulation because of the curved shape of the neck region in patients.

The resistive layer 350 is attached to the conductive layer 366 via a spacer layer 356. The spacer layer 356 includes materials for attaching the resistive layer 350 to the conductive layer 366 and materials for insulating the conductive layer 366 from other portions of the force responsive element 302. The spacer layer 356 may include adhesive strips 352 to attach the resistive layer 350 to the conductive layer 366. The spacer layer may also include a plastic cover 354 which covers and insulates the conductive traces 360 on conductive layer 366.

The force sensitive element 202 and 302 may include additional layers for providing further functionality such as padding, insulation and attachment. For example, layers 356 and 366 may be attached together using connectors 368. As another example, force responsive element 302 includes an adhesive layer (not shown). The adhesive layer may be attached to the bottom of conductive layer 366 such that when positioned on a patient the adhesive layer attaches to the skin of the patient. In certain embodiments, the adhesive layer may be disposed on top of layer 350. In such embodiments, the force responsive element 302 may attach to the user's fingers thereby allowing the user to reposition their fingers as desired for the medical procedure. In certain embodiments, the force responsive layer 302 may include one or more layers of cushioning or padding. In such embodiments, the additional layers of padding may be positioned either above layer 350 or below layer 366.

Additionally and optionally, the force responsive element 202 and 302 may be disposable. In particular, the force responsive element 302 may further include materials that are disposable such that for each use the medical personnel may use a new force responsive element 302 after disposing the old one. In such embodiments, the force responsive element 302 may be connected to a base unit (such as base unit 204) via a removable connector. A portion of such a removable connector may be connected to the conductive traces 360, and another portion of the removable connector may be connected to the respective base unit. After performing the procedure, the force responsive element 302 may be disconnected from the base unit and discarded. A new force responsive element 302 may then be attached to the same base unit for further uses.

Although described with respect to electrical resistance, the force responsive element 302 may include other types of tactile or touch responsive sensors. For example, the force responsive element 302 may include materials with a property, including at least one of an electrical property, magnetic property, optical property, physical property, and chemical property, that changes with touch or tactile force. The force responsive element 302 may include mechanically based sensors, resistive based sensors, capacitive based sensors, magnetic based sensors, optical based sensors, optical fiber based sensors, piezoelectric sensors, piezoresistive sensors, strain gauges, and silicon based sensors.

In certain embodiments, the force responsive element 202 and 302 may include any suitable device for detecting a measuring contact force at a certain point. For example, the force responsive element may include any device suitable for measuring tactile and touch responses. The force responsive element may also include further sensors for measuring texture, slip, impact and other contact conditions and are configured to generate force and position signatures that can be used to identify the state of manipulation.

Figure 4:
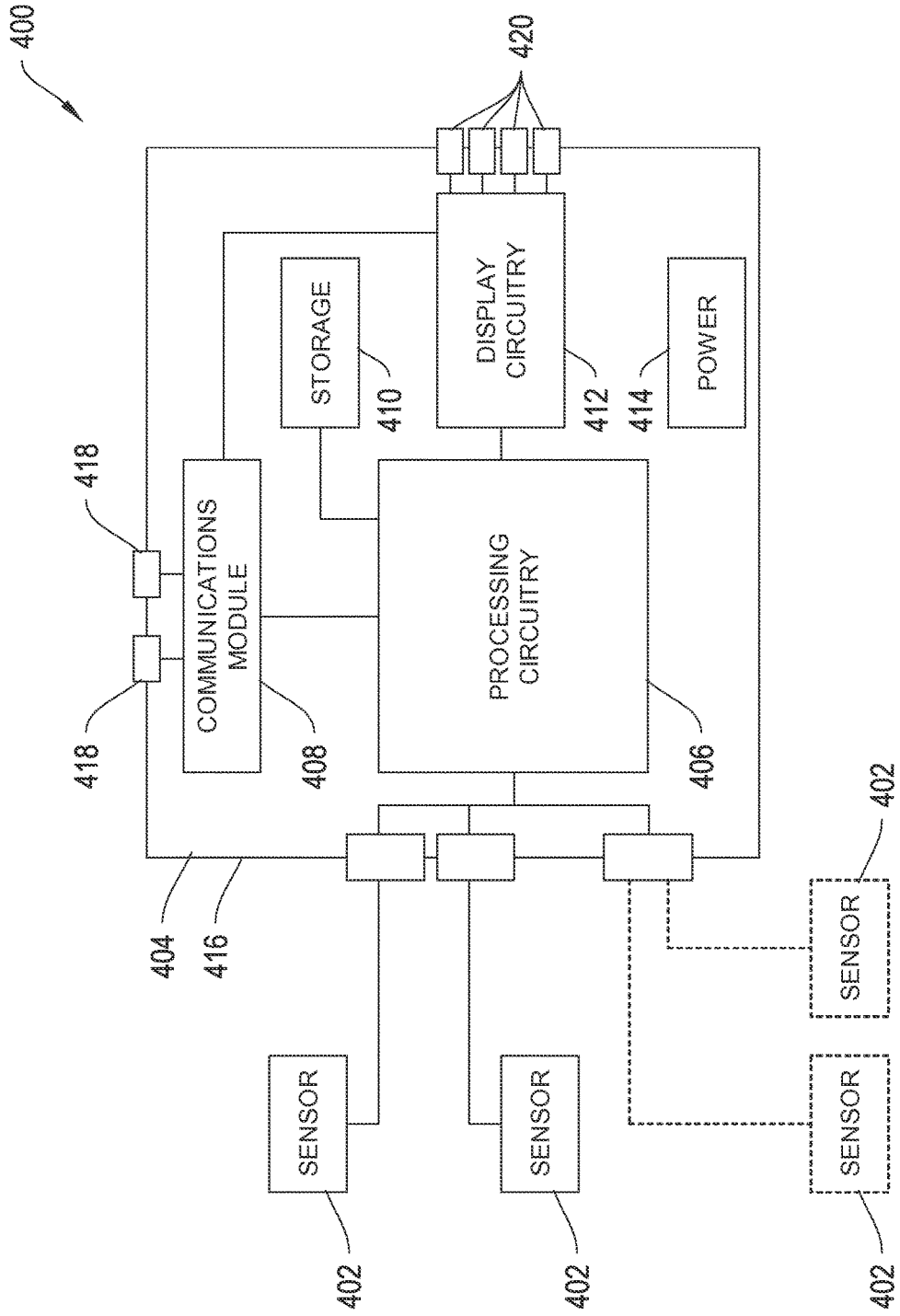
FIG. 4 depicts a block diagram of a force monitoring system, according to an illustrative embodiment of the invention.

As noted with reference to FIG. 2, the force responsive element 202 (and force sensitive resistor 302) may be connected to a base unit 204 having circuitry for measuring and displaying the applied force. FIG. 4 depicts a block diagram of a force monitoring system 400 showing both the force responsive element 202 and the base unit 204, according to an illustrative embodiment of the invention. The force monitoring system 400 includes a plurality of sensors 402 (similar to force responsive elements 202 and 302) connected to a base unit 404 (similar to base unit 204). The base unit 404 includes processing circuitry 406, display circuitry 412, storage 410, power supply 414 and communications module 408. The base unit 404 further includes indicators 420 (e.g., LEDs) and ports 418. The base unit 404 includes housing 416 sized and shaped to enclose the circuitry and accommodate the indicators 420 and ports 418. The housing 416 may be a sized and shaped to attach to a user's body (e.g., wrist, arm or hip) such that the user can perform the medical procedure with one hand and simultaneously monitor applied force on the base unit. The base unit 404 additionally may include one or more switches and other electrical components as desired.

The processing circuitry 406 includes one or more electrical circuits having electrical components, which when connected to the sensors (or force responsive elements) 402 are configured convert the amount of applied force on the sensors 402 to an electrical value, such as a voltage or a current. The processing circuitry 406 may include further signal processing circuitry for calibrating and reducing noise from the electrical signal.

The electrical signal from the processing circuitry 406 may be sent to the display circuitry 412 having one or more electrical circuits having electrical components for translating the electrical value of the applied force to a visual display useful to a user or medical personnel. In one example, the display circuitry 412 is connected to a set of LEDs 420 capable of illuminating when a certain amount of force is applied. The display circuitry 412 may be configured to operate an LCD or any other visual display unit. In certain embodiments, the base unit 404 is connected to an external computer unit and the display circuitry 412 communicates with the external computer unit (such computer systems described with reference to FIG. 7) via communication module 408 and ports 418. In such an embodiment, the amount of applied force may be displayed, recorded and stored on the external computer unit.

In certain embodiments, the base unit 404 may be a stand-alone unit having circuitry specifically designed for use with the force-responsive elements. Such circuitry is shown and described with reference to FIG. 5. In other embodiments, the base unit may be any general purpose computing device as shown and described with reference to FIG. 7.

Figure 5:
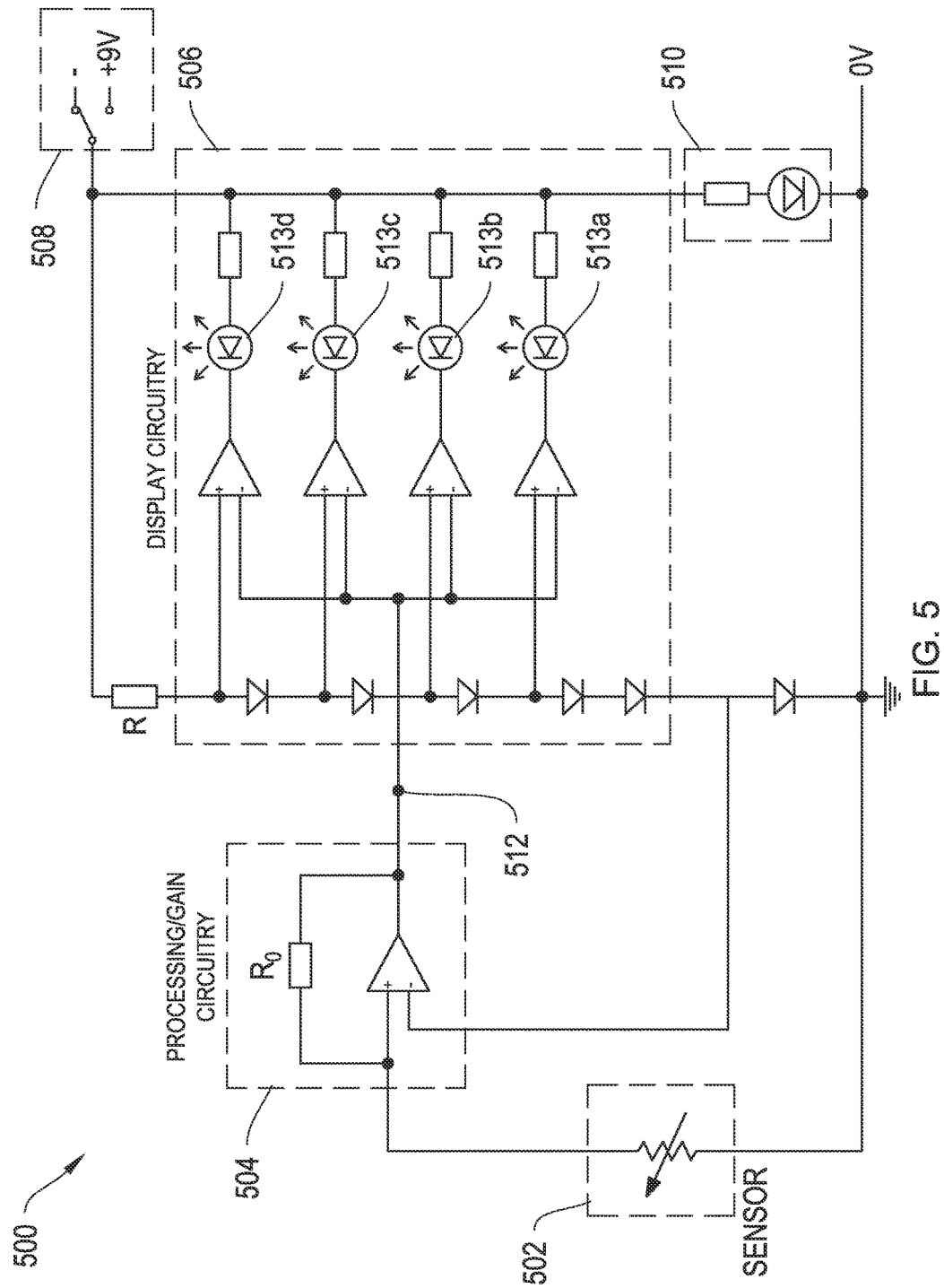
FIG. 5 depicts an exemplary circuit diagram of a force monitoring system, according to an illustrative embodiment of the invention.

FIG. 5 depicts an exemplary electrical circuit 500 for a base unit to be used in connection with a force sensitive resistor 302 shown in FIG. 4. In particular, the force sensitive resistor 302 may be modeled as a variable resistor 502 connected to a processing circuitry 504 and a display circuitry 506. The circuitry is powered by power supply 508. In certain embodiments, the resistance of sensor 502 may be inversely proportional to the force applied to it. It may be desirable to obtain an electrical voltage that is directly proportional to the force on sensor 502. In such embodiments, the processing circuitry 504 includes an operational amplifier and a resistor in a feedback loop. In circuit 500, the voltage at location 512 may be directly proportional to the force on the sensor 502 and inversely proportional to its resistance. The voltage at location 512 is then sent to the display circuitry 506.

The display circuitry 506 may include a plurality of stages corresponding to different values of the voltage at location 512. Each of these stages includes an operational amplifier arranged in a comparator configuration to compare the voltage at location 512 with different reference voltages. As the force on the sensor 502 increases, the voltage at location 512 increases. As the voltage at location 512 increases, different ones of LEDs 513a-513d may illuminate. For example, when the force applied on sensor 502 is too low, LEDs 513a and/or 513b may light up. However, when the force applied on sensor 502 is too high, LED 513d may light up. In such an example, when the force applied on sensor 502 is just right, LED 513c may be illuminated.

The circuit 500 may be calibrated to provide the correct force information for a specific medical procedure. For example, as noted above, when performing the Sellick Maneuver, the appropriate amount of pressure may be about 30 N. In such an example, the sensor 502 may be combination of two sensors 502 disposed on either side of the cricoid cartilage and the appropriate amount of pressure on each sensor 502 may be 15 N. The various circuit components in circuit 500 may be selected such that when a user applies this correct amount of force, LED 513c may light up. If the user applies a force greater than 15 N on each sensor 502, then LED 513d may light up. Alternatively, if the user applies a force less than 15 N on either sensor 502, then LEDs 513a and/or 513b may light up. Any number of circuit components in circuit 500 may be selected as desired to light up any number of LEDs in any combination as desired without departing from the scope of the disclosure. In certain embodiments, the base unit may include two circuits, each similar to circuit 500 for each of two sensors.

In certain embodiments, it may be desirable for a user, using the systems and methods described herein, to adjust or recalibrate the base unit to monitor a different value of pressure or force. For example, for pediatric patients or neonate patients, the amount of force to be applied on the cricoids cartilage during the Sellick Maneuver may be less than 30 N. In such embodiments, gain circuitry 504, and processing circuitry 406 in general, may include one or more components to allow a user to calibrate and thereby select the level of amplification or gain. For example, the gain circuitry 504 may include a selector switch and one or more variable components (e.g., variable resistors) for adjusting the voltage at location 512. Similarly, display circuitry 506, and display circuitry 412 in general, may include one or more components to allow a user to calibrate and thereby select the level of pressure or force required to illuminate the one or more display indicators. For example, the display circuitry 506 may include a selector switch (which may be the same as, or connected to, the selector switch described above with reference to the gain circuitry 504) and one or more variable components for adjusting the level at which the LEDs 513 are illuminated.

The base unit 404 or 500, in general, may include additional switches and/or electrical and/or electronic components to allow the user to vary parameters of components in the processing circuitry 406 and display circuitry 412. For example, the housing 416 of base unit 404 may include one or more selector switches or buttons to allow a user to select different pressure options: low pressure (for pediatric and neonate patients), medium pressure, and high pressure. Depending on the user's selection, the display on the base unit 404 may illuminate differently. For example, in circuit 500, when the user selects medium pressure, the LED 513b may be assigned to illuminate when the force applied is about 30 N. However, when the user selects low or high pressure, the LED 513b may be assigned to illuminate when the force applied is less than or greater than 30 N, respectively.

In certain embodiments, the circuit 500 may include additional circuit components as desired to perform other helpful functions. For example, there may be some variability in the electrical and force characteristics of force sensitive resistors, even those of the same shape and size. To compensate for this variability, the design of circuit 500 may need to additionally include a matching network. A matching network is typically an interface of electrical components placed between the sensor and the rest of the device, such that the characteristics of the sensor appear to the device to be the same as a reference standard. The use of an adaptable matching network may allow sensors with variations in their characteristics to be used by a device as if they were uniform in their characteristics.

In certain embodiments, the base unit 404 or circuit 500 may include circuitry for tracking and maintaining the amount of time pressure or force is applied by a user. The base unit 404 may also include circuitry (e.g., audio, video or vibration alarm) for notifying the user (while the user is applying pressure) when a threshold amount of time has elapsed. The base unit 404 may further include circuitry for allowing a user to program the desired amount of time, pressure and any other relevant parameter in relation to the procedure being administered. For example, during a coronary catheterization, it may be desirable to apply a certain amount of pressure on the groin region for about 30 minutes. The base unit 404 may include circuitry for allowing a user to manually set the time to 30 minutes. In certain embodiments, the base unit 404 may include circuitry for allowing a user to select the "coronary catheterization procedure" from a menu of procedure options, thereby automatically select a threshold time of 30 minutes. The base unit 404 may include a display for allowing a user to view the time lapsed and/or remaining time left in the procedure.

Figure 6:
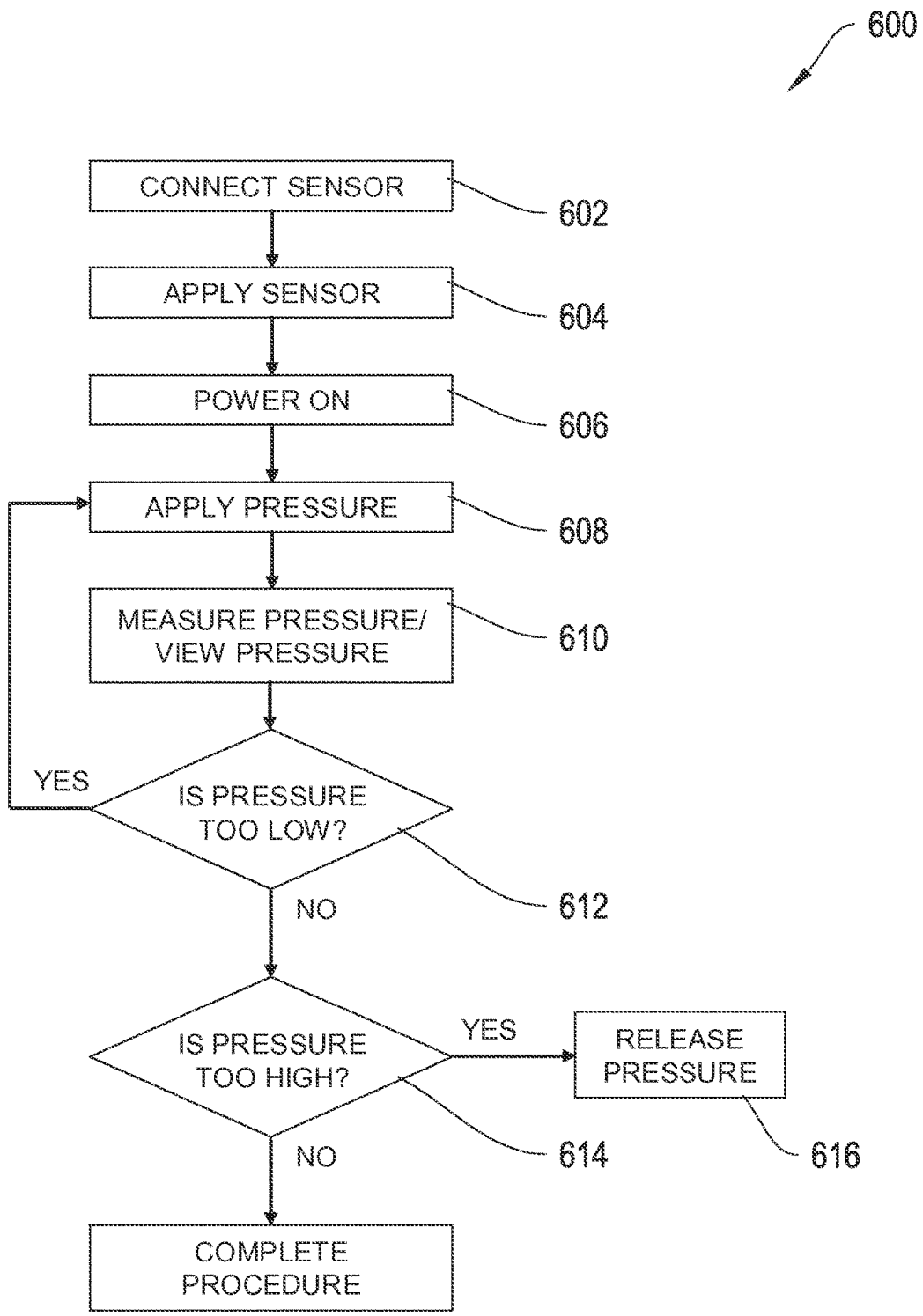
FIG. 6 depicts a process for monitoring force applied during a medical procedure, according to an illustrative embodiment of the invention.

The systems described herein may be used to monitor force in connection with any procedure as desired. FIG. 6 depicts one such process for monitoring force applied during a medical procedure, according to an illustrative embodiment of the invention. In particular, a sensor or force responsive element such as element 202, 302 or 402 is connected to a base unit 204 or 404 (step 602). The sensor or force responsive element is then applied or disposed on the anatomical feature on which medical procedure will be applied (step 604). For example, the sensor may be disposed on the neck region for procedures involving laryngeal manipulation. The power to the base unit and sensor is turned on (step 606) and the user can monitor, on the base unit, the amount of force applied (step 610). The user, based on the displayed information, can then determine if more or less force needs to be applied (steps 612, 614). Based on this determination, the user may increase or decrease force by tightening or releasing their grip (step 608, 616).

As noted earlier, although the systems and methods described thus far were discussed with reference to systems and applications adapted to monitor the application of pressure on the cricoid cartilage or the neck region, it will be understood that these systems and methods may be employed to help any individual monitor and visualize information about applied force or pressure in any scenario.

As another example, the systems and methods described thus far may be employed to monitor the force or pressure applied in regions of bony prominence to prevent the formation of pressure ulcers or decubitus ulcers, and alert medical personnel when a patient may need repositioning or when the likelihood of ulcer formation exceeds a threshold. Similar to systems and methods for monitoring cricoid pressure described with reference to FIGS. 1-6, the systems and methods described herein for the reduction of pressure ulcers may include piezoresistive elements connected to signal processing circuitry for measuring and monitoring the pressure on regions of bony prominences. FIG. 7 depicts a block diagram of a pressure monitoring system, according to an illustrative embodiment of the invention. In particular, the system shown in FIG. 7 includes four sensors 402a-402d connected to a base unit 404. The sensors 402a-d and the base unit 404 may be similar to those described with reference to FIGS. 3 and 4. Sensors 402a-d may be attached to a patient's body and may be positioned over a region of bony prominence including at least one of sacrum, coccyx, heel, hip, ankle, buttock, earlobe, occiput, chin, elbow, scapula, and knee. Base unit 404 may be a handheld device and may include, among other things, a wireless communication circuitry.

The wireless communication circuitry (or communication module 408 shown in FIG. 4) may be configured to collect, packetize and wirelessly transmit raw or processed data from the sensors and/or the processing circuitry. For example, the wireless communication circuitry may be configured to transmit raw voltage or current measurements obtained from the processing circuitry or processed pressure measurements determined by the processing circuitry (As used herein, the term "wireless" means data is transferred to and/or from the device over a wireless medium.) The base unit 404 may also include an integrated or internal transceiver or network interface card (NIC) capable of exchanging data via a wired communications medium, e.g., an Ethernet cable. The base unit 404 may additionally sense and transmit various types of non-pressure data, such as battery-level status data, loose-lead status data, and patient location data. The base unit 404 may transmit and receive data from a computer station such as computer 702, mobile tablet device 704 and smartphone 706.

Generally, the base unit 404 may communicate bi-directionally with any number of radio transceivers, referred to as access points (AP). The APs may use one of various types of wireless protocols and standards such as time division multiple access (TDMA), code division multiple access (CDMA), 802.11, Wifi, Bluetooth, cellular, GPRS, LTE, EVDO, WiMax, and the like. In one mode of operation, each AP can communicate with multiple base units 404 at-a-time. The APs may be spaced apart from one another throughout the hospital or healthcare facility to provide a "cell-like" coverage area which consists of overlapping zones of coverage.

Different APs of the system may operate (i.e., transmit and receive data) on a different RF frequency channels ("frequencies"). However, APs that are sufficiently spaced apart to avoid interference with one another may operate on like frequencies. Although the base units 404 and APs shown in FIGS. 4 and 7 are of the type, which communicate by radio frequency (RF), the system may also include "hardwired" base units 404 and APs which communicate over hardwire connections.

The computer stations may include conventional desktop computer systems 702 and/or portable communications devices 704 and 706. The portable communications devices 704 and 706 may include a pda, portable computer, cellular telephone, smart phone, digital tablet, wireless communications device, and the like. The computer station may utilize one or more communications protocols such as 802.11, WiMax, Wifi, GPRS, CDMA, LTE, pager protocols, Bluetooth, a PAN protocol, a wireless LAN protocol, a wide area network (WAN) protocol, or any suitable wireless protocol to enable communications with one or more base units 404 and with each other.

Figure 8A:
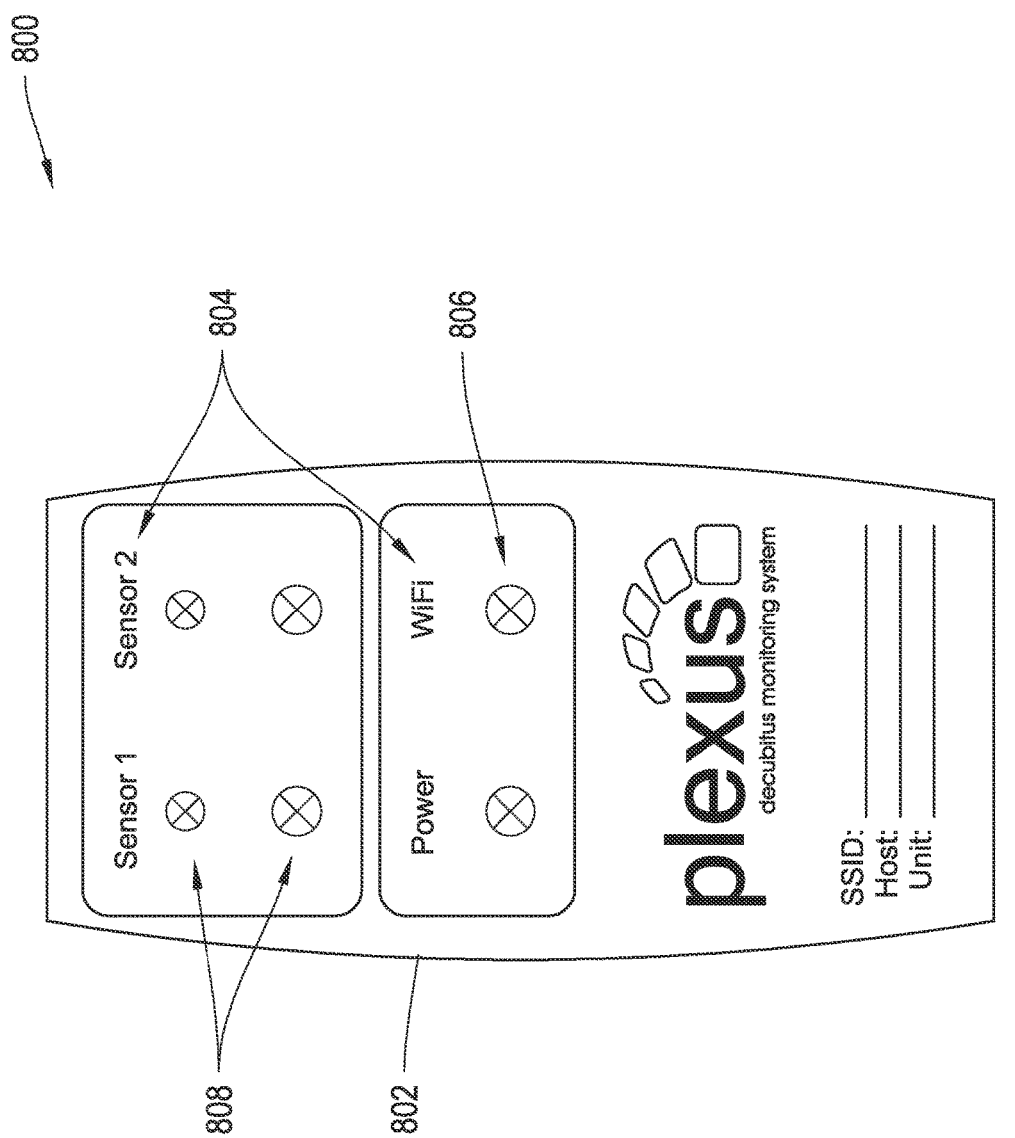
Figure 8B:
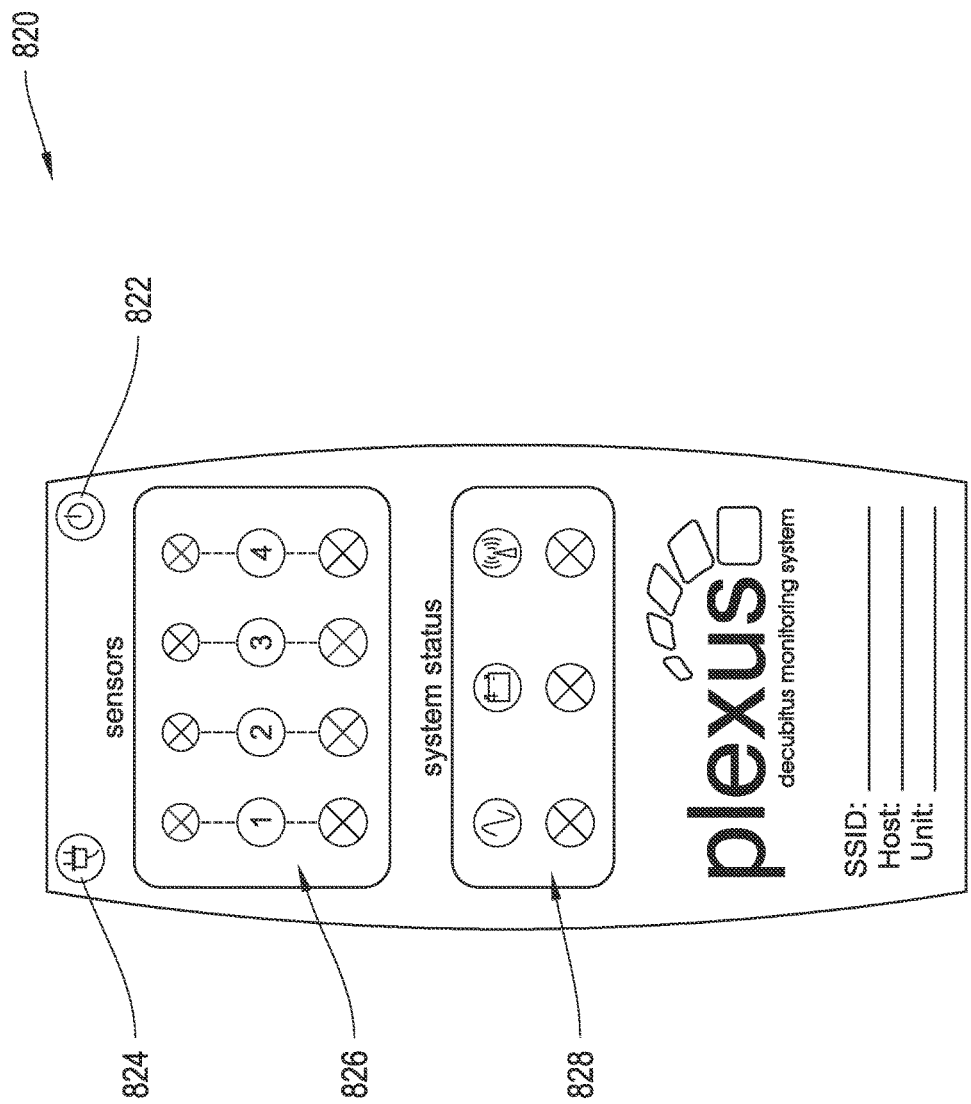

FIGS. 8A-8C depict exemplary base units, according to an illustrative embodiment of the invention. Base unit 800 described with reference to FIG. 8A includes housing 802 and circuitry, disposed within the housing 802, for receiving data from two sensors. The base unit 800 includes LEDs 808 showing the status and/or measurements obtained from each of the two sensors. The base unit 800 also includes a power indicator and a network connectivity indicator 806. The housing 802 may include one or more labels 804 to identify the LEDs and to provide additional information about the host and unit identification. Base unit 820, shown in FIG. 8B may be similar to base unit 800, with the exception that base unit 820 is configured to receive and process measurements from four sensors. Section 826 of the housing may be configured for displaying information from each of the four sensors and section 828 may be configured for displaying system status. In addition, base unit 820 includes a power button 822 and an external adapter slot 824. Base unit 840 may be similar to base units 800 and 820, wich the exception that base unit 840 includes an additional system status EKG light 842. In particular, base unit 840 may include signal processing circuitry for receiving electrocardiogram (EKG) signals from one or more EKG sensors also connected to the base unit.

Although the base unit is described herein as a stand alone device, in certain embodiments, certain circuitry within the base unit may be incorporated into an adapter device, which in turn may be connected to a conventional mobile device such as a smartphone or tablet. In such embodiments, the base unit and the sensors may be coupled with conventional mobile devices for display and processing of sensor pressure data.

Figure 9A:
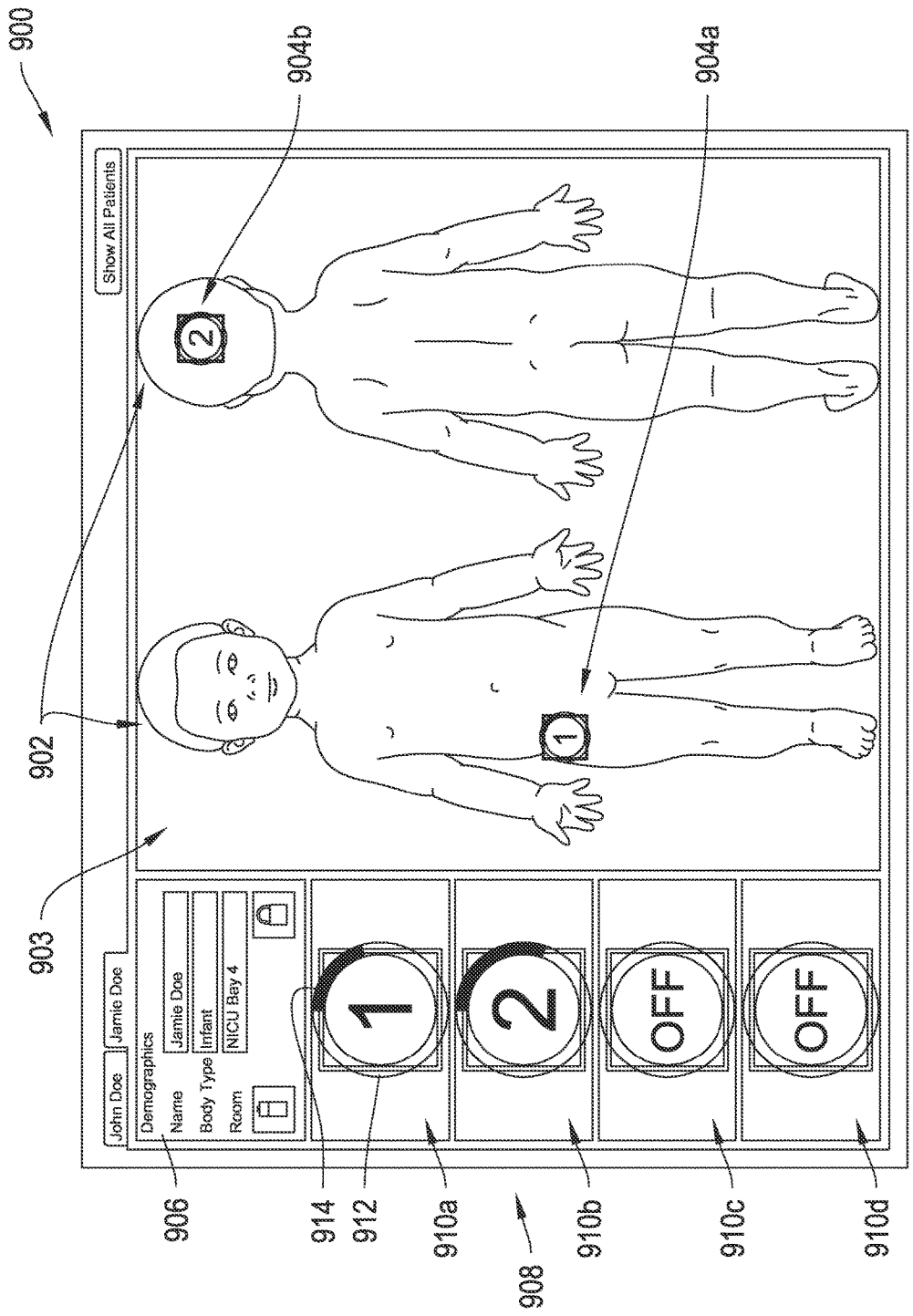
FIGS. 9A-9C depict screenshots of a pressure monitoring system, according to an illustrative embodiment of the invention.
Figure 9B:
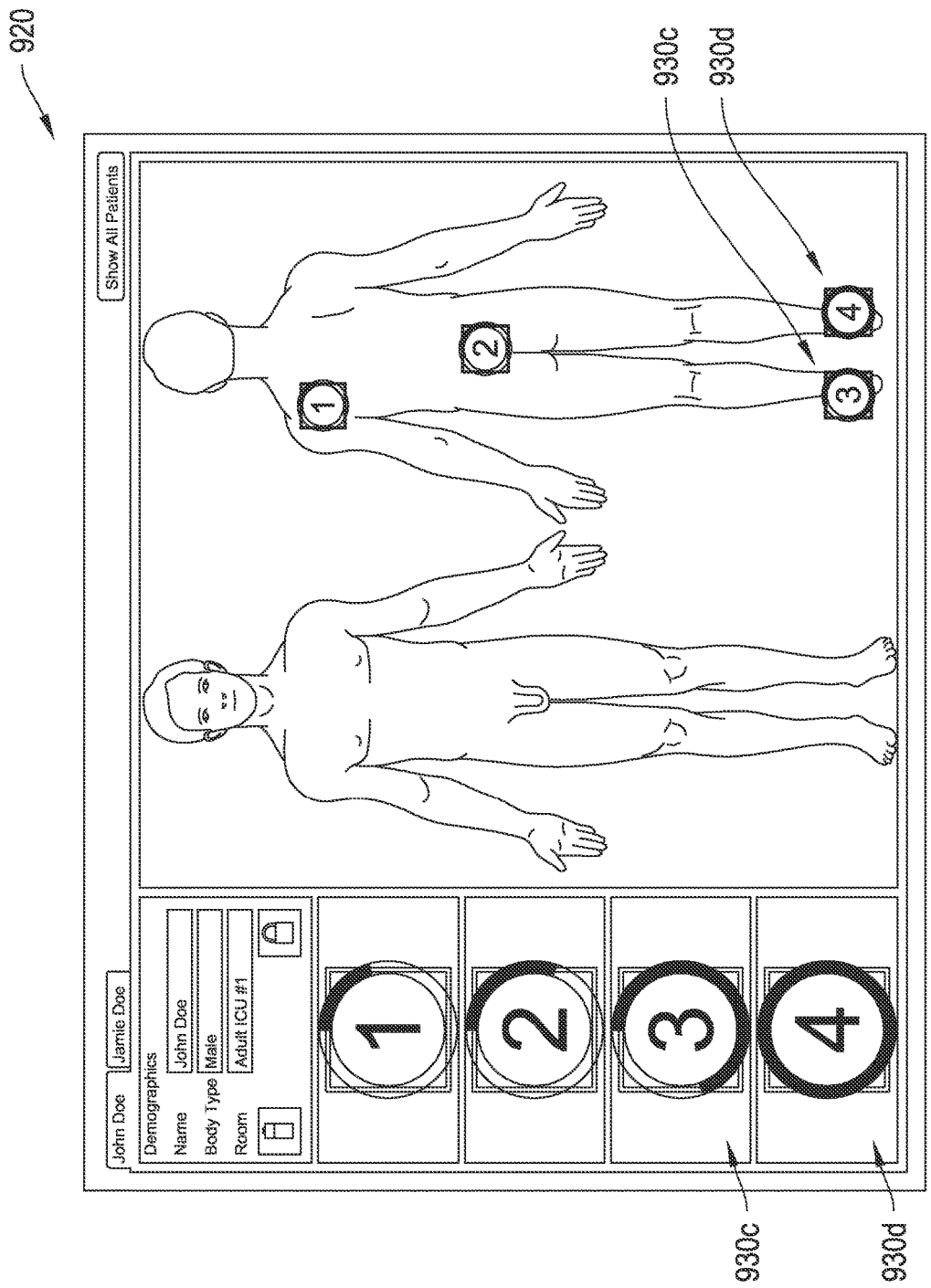
Figure 9C:
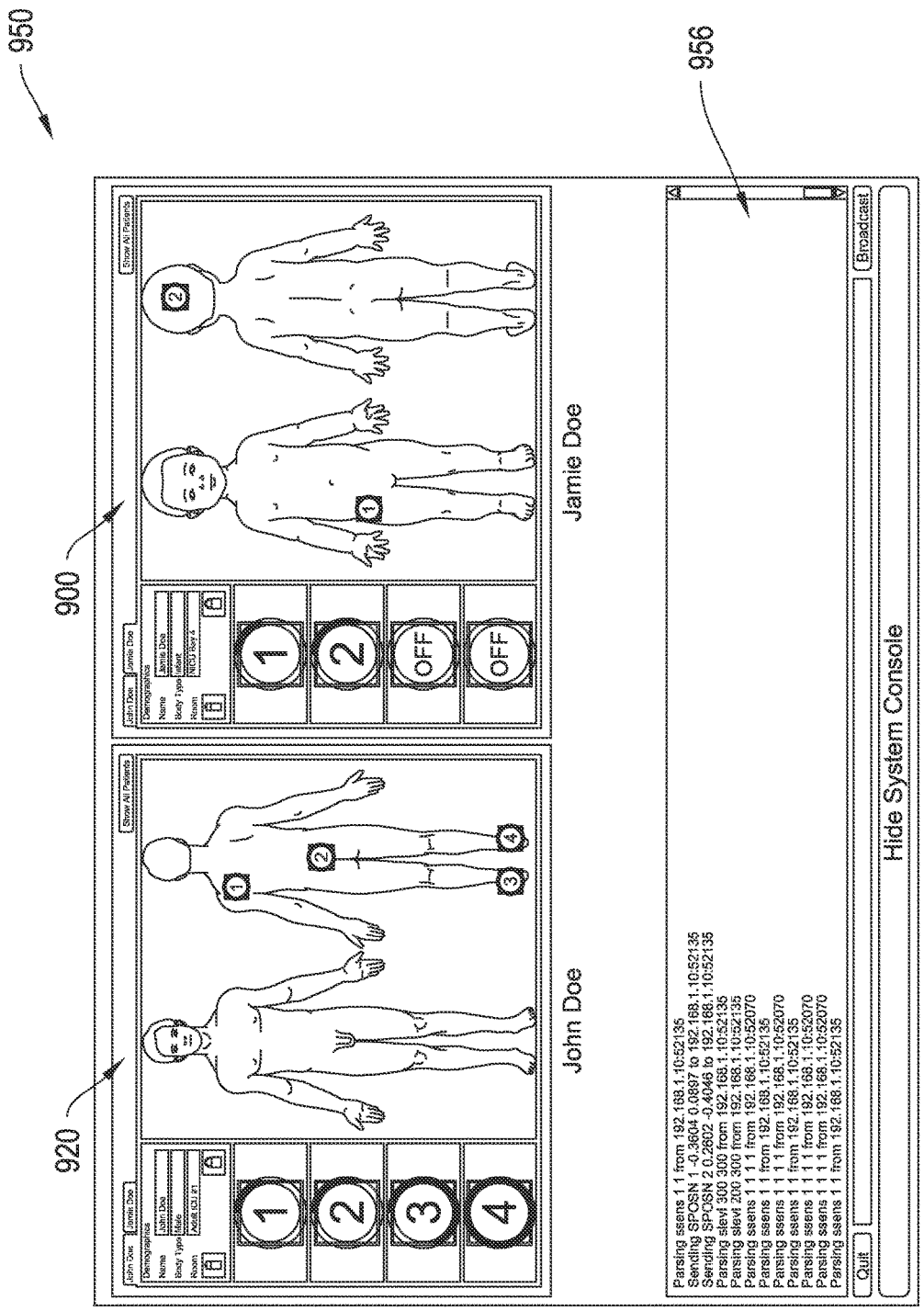

As noted earlier, the base unit 404 may communicate with one or more computer stations. The computer station may include a circuitry for running and displaying a user interface application for displaying pressure-related information to a user. FIGS. 9A-9C depict screenshots of a pressure monitoring system, according to an illustrative embodiment of the invention. FIG. 9A depicts screenshot 900 showing two sensors placed on a hospitalized child. In particular, the user interface includes a visual depiction of a human child 902 from the front and the back. Overlaid on the visual depiction, the screenshot 900 includes a visual representation (e.g., graphic or icon) of the position of a sensors. One graphic 904a shows a sensor positioned on the side of a child and another graphic 904b shows a sensor positioned on the back of a child's head. The screenshot also includes a listing of each of the sensors 910a-d that may be connected or connectable to the base unit. Graphics 910a-b show that two sensors are connected and operational while the two sensors 910c-d are currently "off" The graphic visual representation of each of the sensors further includes an indication of the alert level for the sensor. For example, graphic 910a-b may change in color depending on the length of time one or more measured pressure values exceed a predetermined threshold. In certain embodiments, the passage of time may be depicted on graphic 910a-d as a wheel 912 that may be filled with color 914. The screenshot further includes patient data information 906.

FIG. 9B depicts a screenshot 920 similar to screenshot 900 of FIG. 9A, with the exception that the patient in FIG. 9B is an adult male and has four sensors positioned on him. The listing on the screenshot 920 no longer has the third and fourth sensor 930c-d as being "off," but instead operational. Screenshot 950 in FIG. 9C depicts a computer station in communication with two base units, one monitoring the formation of pressure ulcers in a child 900 and another monitoring the formation of pressure ulcers in an adult 920. The user interface may include any number of connected sensors from any number of patients through any number of base units with departing from the scope of the present disclosure. In addition, screenshot 950 includes information about the wireless connectivity in section 956.

Figure 10:
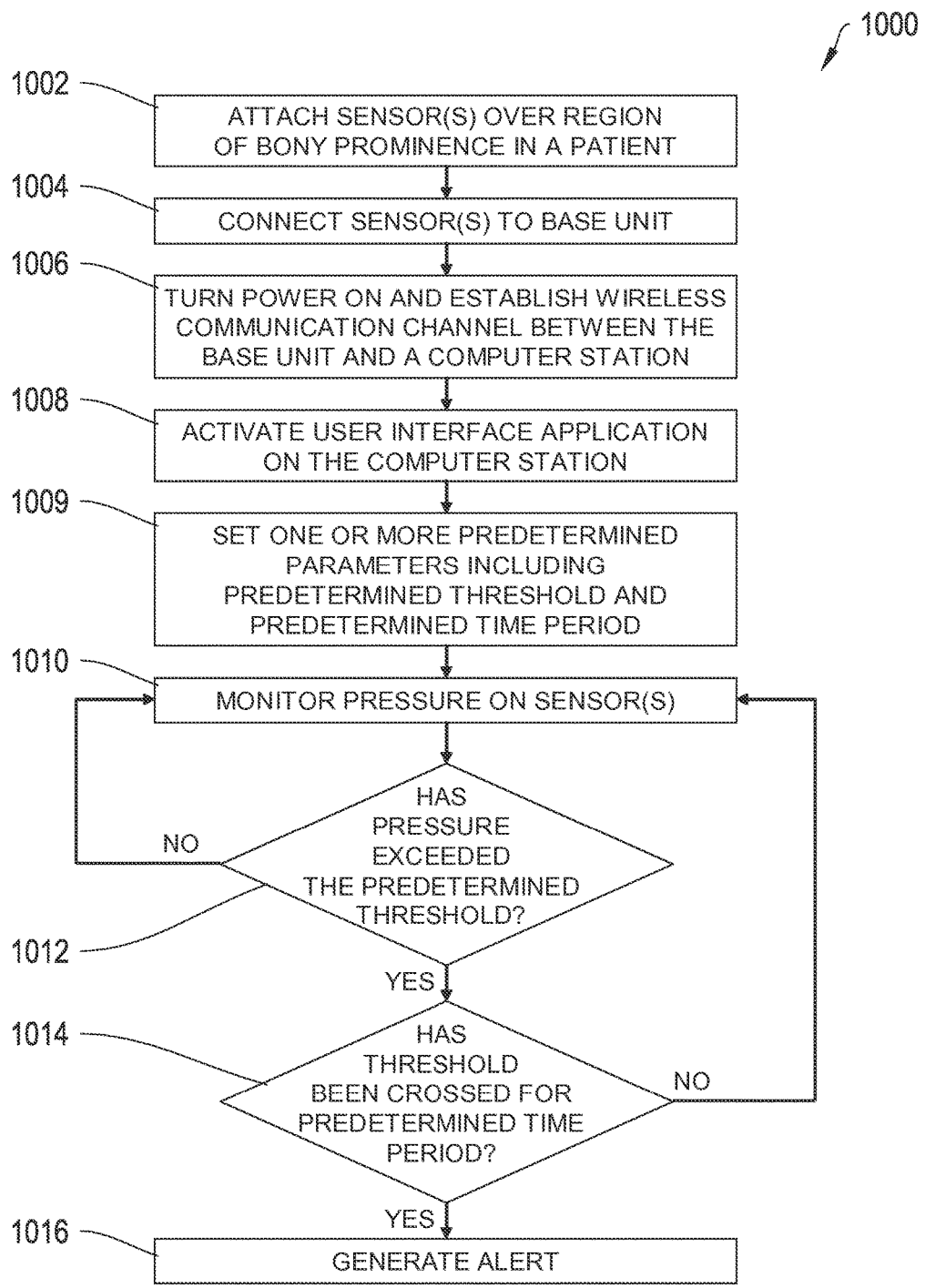
FIG. 10 depicts a process for monitoring pressure applied on a region of bony prominence, according to an illustrative embodiment of the invention.

The systems described herein may be used to monitor the formation of pressure ulcers. FIG. 10 depicts such a process 1000 for monitoring pressure applied on a region of bony prominence, according to an illustrative embodiment of the invention. The sensors (such as sensors 402 and 302) are positioned over a region of bony prominence in a patient (step 1002). In certain embodiments, the sensors may be attached to the skin of the patient and/or attached to portions of the underlying mattress, bedding, or cushioning material. The sensors may be combined with dressing, which in turn may be applied over a portion of the patient's body. In certain embodiments, the sensors may be integrally formed within the dressing material. In step 1004, the sensors may be connected to the base unit (similar to base unit 404, 800, 820 and 840).

The sensors may be connected via a wired connection or a wireless connection with the base unit. At step 1006, the base unit may be powered on and the base unit may (automatically or manually) establish a wireless communication channel or session with a computer station (similar to computer stations 702, 704 and 706). Once the communication session is established, a user interface session may be activated via a user interface application on the computer station (step 1008). In particular, in certain embodiments, a user may start running an executable version of a pressure monitoring computer application on the computer station. The pressure monitoring computer application may be part of a larger computer application for recording data from other patient monitoring devices. The patient monitoring computer application may include a user interface (similar to user interfaces 900, 920 and 950) configured to allow a user to add, remove, edit or otherwise manipulate measured and/or processed data. In addition, the user interface may be configured to allow a user to specify and manipulate the visual representation of the position of the sensors. For example, turning to FIG. 9A, a user may drag and drop the sensor graphics 904a and 904b as desired to indicate the location and positioning of the sensor on the child. The computer application may be configured to correlate the selected position of the sensor with other physiological and medical information associated with the patient.

The patient monitoring computer application installed on a computer station may include several user adjustable features including a feature for allowing the user to set predetermined threshold values of pressure, which when exceeded may indicate the increased likelihood of the formation of a pressure ulcer. For example, the user interface may include a text box to allow a user to enter a value of pressure (e.g., 32 mm Hg) that when exceeded may result in occlusion of capillary flow causing ischemic injury and extravasation of fluids, cells, and protein. Generally, the predetermined threshold may be based on a number of factors including those intrinsic to a patient. For example, the predetermined threshold may be based on patient information such as age, chronic disease, impaired mobility and limited activity, disease condition, sensory impairment and the like. The predetermined threshold may also be based on extrinsic factors such as sensor perception (or the patient's ability of detect and respond to discomfort, pain or pressure), skin moisture, physical activity, patient mobility, patient nutrition, and friction and shear experienced by the patient. In certain embodiments, the predetermined threshold may be automatically determined based on information received by the computer station from other devices, computers and patient monitors.

Another example of a user adjustable feature may include a predetermined time period, and the user interface may be configured with visual elements such as text boxes to allow a user to provide a predetermined time period that when exceeded may indicate the increased likelihood of the formation of a pressure ulcer. In certain embodiments, the predetermined time period may be linked to the predetermined threshold in that the time period may indicate a length of time during which the pressure on the patient's body exceeds the predetermined threshold. In certain embodiments, the predetermined time period may be a fixed window of time, while in other embodiments, the predetermined time period may be a variable time period. Generally, the predetermined time period and the predetermined threshold may be selected as desired without departing from the scope of the present disclosure.

At step 1010, the base unit and the computer station may begin monitoring, either automatically or upon user request, the pressure on the sensors. If the pressure exceeds the predetermined threshold (step 1012), then the computer station determines whether this threshold has been crossed for a predetermined time period (step 1014). If it is determined that the threshold has been crossed for the predetermined time period, either continuously or in bursts, then the user interface on the computer system may generate an alert (step 1016). In certain embodiments, even if the predetermined time period has not been exceeded, the user interface may provide one or more intermediate alerts to a user indicating an increasing likelihood of ulcer formation. Turning to FIG. 9A, the user interface may indicate whether the predetermined threshold is exceeded at a sensor by changing the color on a visual element such as graphic 910a. For example, when the threshold is exceeded, the graphic 910a may turn red and start blinking In certain embodiments, depending on the extent to which the pressure on the sensor has exceeded the predetermined threshold, the graphic 910a may gradually turn from green (indicating the pressure is below a threshold) to yellow (indicating the pressure has just exceeded the threshold) to red (indicating that the pressure has substantially exceeded the threshold).

As noted above, an alert may be generated upon determining that the threshold has been crossed for a predetermined period of time (steps 1014 and 1016). The graphic 910a in FIG. 9A also shows a wheel 912 and a progress bar 914. The wheel 912 and/or progress bar 914 may represent the predetermined time period. In certain embodiments, an alert may be shown or sounded when the progress bar 914 substantially or completely fills the wheel 912. The graphic 910a may also change color as the progress bar 914 progressively fills the wheel 912. Generally, an alert may include any suitable visual, audio or tactile alert without departing from the scope of the present disclosure. An alert may also be sent from one computer station to a mobile device. For example, a nurse may be located in another part of the hospital and may not have access to a computer station. In such an example, the computer station may generate and send a page or text message alert to the nurse.

Figure 11:
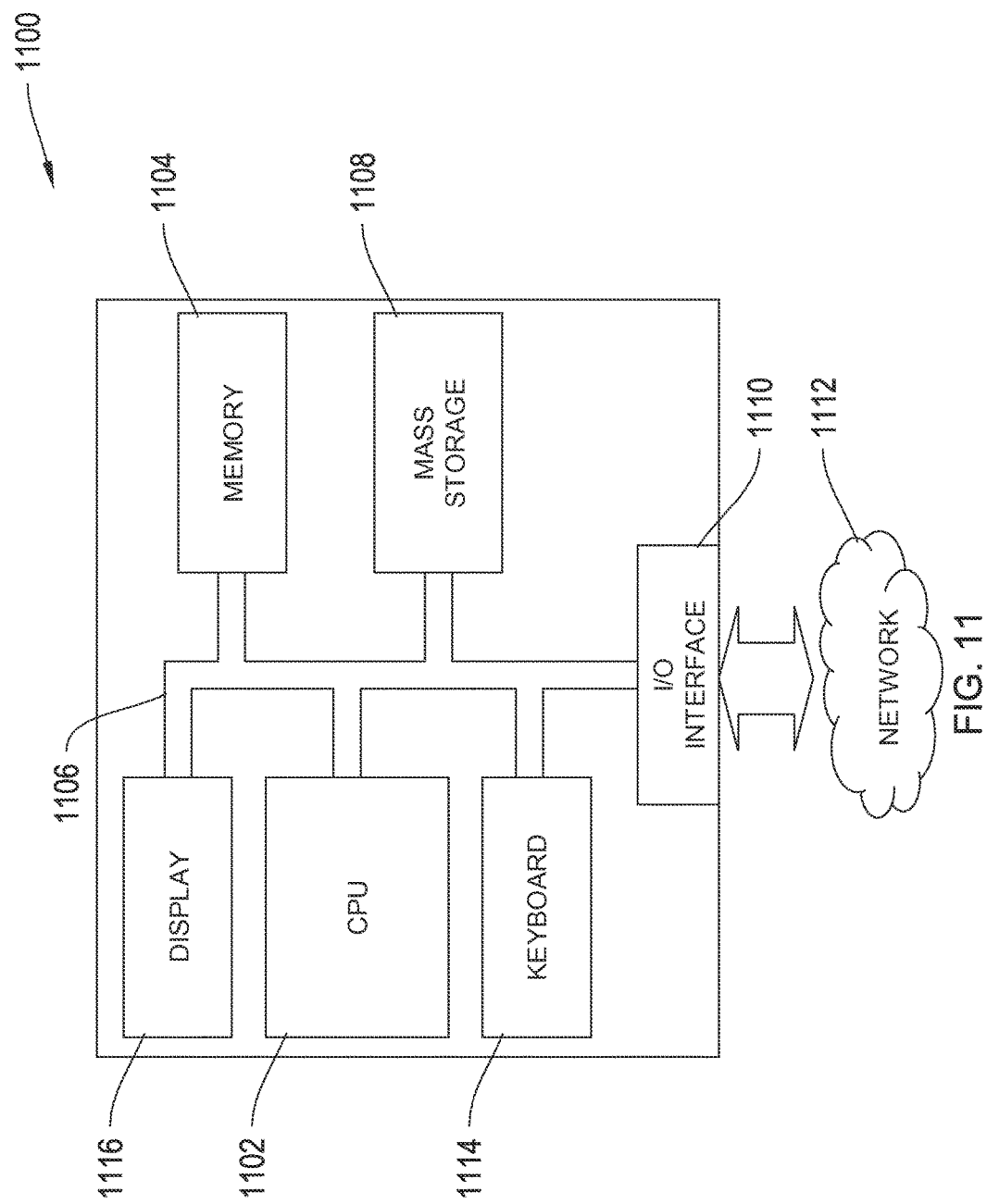
FIG. 11 depicts a functional block diagram of an exemplary general purpose computer system to be used in connection with or as a base unit, according to an illustrative embodiment of the invention.

As noted above, the base unit may be any general purpose computing device as shown and described with reference to FIG. 11. FIG. 11 includes a functional block diagram of an exemplary general purpose computer system, e.g., base unit 1100, for performing the functions of base unit 204 or 404. The exemplary computer system 1100 includes a central processing unit (CPU) 1102, a memory 1104, and an interconnect bus 1106. The CPU 1102 may include a single microprocessor or a plurality of microprocessors for configuring computer system 1100 as a multi-processor system. The memory 1104 illustratively includes a main memory and a read only memory. The computer 1100 also includes the mass storage device 1108 having, for example, various disk drives, tape drives, etc. The main memory 1104 also includes dynamic random access memory (DRAM) and high-speed cache memory. In operation, the main memory 1104 stores at least portions of instructions and data for execution by the CPU 1102.

The mass storage 1108 may include one or more magnetic disk or tape drives or optical disk drives or memory sticks, for storing data and instructions for use by the CPU 1102. The mass storage system 1108 may also include one or more drives for various portable media, such as a floppy disk, a compact disc read only memory (CD-ROM), or an integrated circuit non-volatile memory adapter (i.e. PC-MCIA adapter) to input and output data and code to and from the computer system 1100.

The computer system 1100 may also include one or more input/output interfaces for communications, shown by way of example, as interface 1110 for data communications via the network 1112. The data interface 1110 may be a modem, an Ethernet card or any other suitable data communications device. To provide the functions of the systems described herein, the data interface 1110 may provide a relatively high-speed link to a network 1112, such as an intranet, internet, or the Internet, either directly or through an another external interface. The communication link to the network 1112 may be, for example, optical, wired, or wireless (e.g., via satellite or cellular network). Alternatively, the computer system 1100 may include a mainframe or other type of host computer system capable of Web-based communications via the network 1112. The computer system 1100 may include software for operating an network application such as a web server and/or web client.

The computer system 1100 also includes suitable input/output ports or use the interconnect bus 1106 for interconnection with a local display 1116 and keyboard 1114 or the like serving as a local user interface for programming and/or data retrieval purposes. The display 1116 may include a touch screen capability to enable users to interface with the system 1100 by touching portions of the surface of the display 1116. Server operations personnel may interact with the system 1100 for controlling and/or programming the system from remote terminal devices via the network 1112.

The computer system 1100 may run a variety of application programs and store associated data in a database of mass storage system 1108. One or more such applications may enable the receipt and delivery of messages to enable operation as a server, for implementing server functions.

The components contained in the computer system 1100 are those typically found in general purpose computer systems used as servers, workstations, personal computers, network terminals, and the like. In fact, these components are intended to represent a broad category of such computer components that are well known in the art. For example, the components contained in the computer system 1100 are those found in mobile devices such as a laptop, PDA, or smartphone. The computer system 1100 may include, among others, a cellular phone, personal digital assistant (PDA), smartphone (such as the Apple® iPhone® manufactured by Apple, Inc., located in Cupertino, Calif.), and a tablet computer or a mobile touch screen computer (such as the Apple® iPad® manufactured by Apple, Inc., located in Cupertino, Calif.).

As discussed above, the general purpose computer system 1100 may include one or more applications that provide patient management and information collection. The system 1100 may include software and/or hardware that implements a web server application. The web server application may include software such as HTML, XML, WML, SGML, PHP (Hypertext Preprocessor), CGI, and like languages.

The foregoing embodiments of the systems and methods described herein may be realized as a software component operating in the system 1100 where the system 1100 is Unix workstation or other type of workstation. Other operation systems may be employed such as, without limitation, Windows, MAC OS, and LINUX. In some embodiments, the systems and methods described herein can optionally be implemented as a C language computer program, or a computer program written in any high level language including, without limitation, C++, Fortran, Java, or Visual BASIC. Certain script-based programs may be employed such as XML, WML, PHP, and so on. Additionally, general techniques for high level programming are known, and set forth in, for example, Stephen G. Kochan, Programming in C, Hay den Publishing (1983). The system 1100 may use a DSP for which programming principles well known in the art.

As stated previously, the mass storage 1108 may include a database. The database may be any suitable database system, including the commercially available Microsoft Access database, and can be a local or distributed database system. The design and development of suitable database systems are described in McGovern et al., A Guide To Sybase and SQL Server, Addison-Wesley (1993). The database can be supported by any suitable persistent data memory, such as a hard disk drive, RAID system, tape drive system, floppy diskette, or any other suitable system. The system 1100 may include a database that is integrated with the system 1100, however, it will be understood by those of ordinary skill in the art that in other embodiments the database and mass storage 1108 can be an external element.

In certain embodiments, the system 1100 may include an Internet browser program and/or be configured operate as a web server. In some embodiments, the client and/or web server may be configured to recognize and interpret various network protocols that may be used by a client or server program. Commonly used protocols include Hypertext Transfer Protocol (HTTP), File Transfer Protocol (FTP), Telnet, and Secure Sockets Layer (SSL), for example. However, new protocols and revisions of existing protocols may be frequently introduced. Thus, in order to support a new or revised protocol, a new revision of the server and/or client application may be continuously developed and released.

In certain embodiments, the systems and methods described herein include a networked-based, e.g., Internet-based, application that may be configured and run on the system 1100. System 1100 may include a web server running a Web 2.0 application or the like. Web applications may use server-side dynamic content generation mechanisms such, without limitation, JavaScript, CGI, PHP, or ASP. In certain embodiments, mashed content may be generated by the web browser via, for example, client-side scripting including, without limitation, JavaScript and/or applets.

In certain embodiments, the systems and methods described herein may include applications that employ asynchronous JavaScript+XML (Ajax) and like technologies that use asynchronous loading and content presentation techniques. These techniques may include, without limitation, XHTML and CSS for style presentation, document object model (DOM) API exposed by a web browser, asynchronous data exchange of XML data, and web browser side scripting, e.g., JavaScript. Certain web-based applications and services may utilize web protocols including, without limitation, the services-orientated access protocol (SOAP) and representational state transfer (REST). REST may utilize HTTP with XML.

The base unit 204 and 404, and system 1100 may also provide enhanced security and data encryption. Enhanced security may include access control, biometric authentication, cryptographic authentication, message integrity checking, encryption, digital rights management services, and/or other like security services. The security may include protocols such as IPSEC and IKE. The encryption may include, without limitation, DES, AES, RSA, and any like public key or private key based schemes.

Variations, modifications, and other implementations of what is described may be employed without departing from the spirit and scope of the disclosure. More specifically, any of the method and system features described above or incorporated by reference may be combined with any other suitable method, system, or device feature disclosed herein or incorporated by reference, and is within the scope of the contemplated systems and methods described herein. The systems and methods may be embodied in other specific forms without departing from the spirit or essential characteristics thereof. The foregoing embodiments are therefore to be considered in all respects illustrative, rather than limiting of the systems and methods described herein. The teachings of all references cited herein are hereby incorporated by reference in their entirety.

The invention claimed is:

1. A system for monitoring force applied during a laryngeal manipulation procedure requiring application of force, the system comprising:
   a first force responsive element, placed on skin of a patient's body, having a property which varies with a force applied by a user on the first force responsive element, the first force responsive element including a force sensitive resistor having:
      a resistive layer,
      a conductive layer,
      a spacer layer positioned between the resistive layer and the conductive layer, and
      an adhesive layer positioned to attach to a finger of the user while the user is performing the laryngeal manipulation procedure; and
   a base unit connected to the first force responsive element and having:
      a memory comprising an association between (i) the laryngeal manipulation procedure and (ii) a threshold level of force for performing the laryngeal manipulation procedure without injuring the patient;
      circuitry arranged to:
         i) receive, from the user, a selection of laryngeal manipulation procedure from a menu of a plurality of medical procedures, wherein each of the plurality of medical procedures requires application of force on the patient's body by the user; ii) retrieve from the memory, based on receiving the selection of the laryngeal manipulation procedure, the threshold level of force; iii) determine an amount of the force applied by the user based on a value of the property of the first force responsive element; and iv) generate for display feedback on the amount of force applied by the user via an indication of the amount of the force applied by the user relative to the retrieved threshold level of force, the base unit being a handheld device configured to be monitored by the user while applying the force.

2. The system of claim 1, wherein the conductive layer includes at least two unconnected conductive traces disposed on a flexible substrate, and wherein the resistive layer is disposed over a gap between the at least two unconnected conductive traces.

3. The system of claim 1, wherein the resistive layer is formed from piezoresistive material.

4. The system of claim 1, wherein the system further comprises a second force responsive element physically attached to the first force responsive element.

5. The system of claim 1, wherein the property includes at least one of an electrical property, magnetic property, optical property, physical property, and chemical property.

6. The system of claim 5, wherein the property includes electrical resistance.

7. The system of claim 1, wherein the indication of the amount of the force applied by the user includes one or more light emitting diodes.

8. The system of claim 7, wherein the one or more light emitting diodes are configured to indicate that the amount of the force applied on the first force sensitive resistor is greater than the threshold level of force.

9. The system of claim 1, wherein the base unit includes wireless communication circuitry arranged to transmit data including at least one of a value of electrical resistance of the force sensitive resistor, a voltage value determined based on the electrical resistance, an electric current value determined based on the electrical resistance, and the amount of the force applied.

10. The system of claim 1, further comprising a computer station having a processor including circuitry arranged to receive, from the base unit, pressure information corresponding to the amount of the force applied on the first force sensitive resistor.

11. The system of claim 10, wherein the processor includes a display and display circuitry arranged to display, on the display, a visual indicator identifying the first force sensitive resistor, and wherein the display circuitry at the processor includes one or more visual indicators for indicating whether the amount of the force applied on the first force sensitive resistor is greater than the threshold level of force.

12. The system of claim 11, wherein the display circuitry is configured for displaying a location of the first force sensitive resistor on the patient.

13. The system of claim 10, wherein the processor includes circuitry arranged to determine whether the amount of the force applied on the first force sensitive resistor is greater than the threshold level of force.

14. The system of claim 13, wherein determining whether the amount of the force applied is greater than the threshold level of force includes determining whether the amount of the force is greater than the threshold level of force for a predetermined period of time.

15. The system of claim 1, wherein the first force responsive element is configured to be positioned on a neck region of a patient.

16. The system of claim 15, wherein the first force responsive element includes an attachment mechanism for positioning on the neck region of the patient.

17. The system of claim 16, wherein the attachment mechanism includes adhesive.

18. The system of claim 6, wherein the base unit includes signal processing circuitry arranged to determine the value of the electrical resistance.

19. A method for monitoring force applied during a laryngeal manipulation procedure requiring application of force, the method comprising:
applying, to skin of a patient's body, a first force responsive element having a property which varies with a force applied by a user on the first force responsive element, the first force responsive element including a force sensitive resistor having:
a resistive layer,
a conductive layer,
a spacer layer positioned between the resistive layer and the conductive layer, and
an adhesive layer positioned to attach to a finger of the user while the user is performing the laryngeal manipulation procedure, wherein the first force responsive element is connected to a base unit connected to the first force responsive element, wherein the base unit has a memory comprising an association between (i) the laryngeal manipulation procedure and (ii) a threshold level of force for performing the laryngeal manipulation procedure without injuring the patient; and
receiving, at the base unit, from the user, a selection of laryngeal manipulation procedure from a menu of a plurality of medical procedures, wherein each of the plurality of medical procedures requires application of force on the patient's body by the user;
retrieving from the memory, based on receiving the selection of the laryngeal manipulation procedure, the threshold level of force;
determining, by the base unit, an amount of the force applied by the user based on a value of the property of the first force responsive element; and
generating for display, at the base unit, feedback on the amount of force applied by the user via an indication of the amount of the force applied by the user relative to the retrieved threshold level of force, the base unit being a handheld device configured to be monitored by the user while applying the force.

20. The method of claim 19, wherein the conductive layer includes at least two unconnected conductive traces disposed on a flexible substrate, and wherein the resistive layer is disposed over a gap between the at least two unconnected conductive traces.

21. The method of claim 19, wherein the resistive layer is formed from piezoresistive material.

22. The method of claim 19, wherein the first force responsive element is physically attached to a second force responsive element.

23. The method of claim 19, wherein the property includes at least one of an electrical property, magnetic property, optical property, physical property, and chemical property.

24. The method of claim 23, wherein the property includes electrical resistance.

25. The method of claim 19, wherein the first force responsive element includes an attachment mechanism for positioning on the neck region of the patient.

26. The method of claim 25, wherein the attachment mechanism includes adhesive.

27. The method of claim 19, wherein the base unit includes signal processing circuitry arranged to determine the value of the electrical resistance.

28. The method of claim 19, wherein the indication of the amount of the force applied by the user includes lighting one or more light emitting diodes.

29. The method of claim 28, wherein the one or more light emitting diodes are configured to indicate that the amount of the force applied on the first force sensitive resistor is greater than the threshold level of force.

30. The method of claim 19, wherein the base unit includes wireless communication circuitry arranged to transmit data including at least one of a value of electrical resistance of the force sensitive resistor, a voltage value determined based on the electrical resistance, an electric current value determined based on the electrical resistance, and the amount of the force applied.

31. The method of claim 19, wherein the first force responsive element is applied to a neck region of a patient.

* * * * *